(12) United States Patent
Ranganathan et al.

(10) Patent No.: US 7,026,466 B1
(45) Date of Patent: Apr. 11, 2006

(54) SEROTONIN-GATED ANION CHANNEL

(75) Inventors: Rajesh Ranganathan, Cambridge, MA (US); H. Robert Horvitz, Auburndale, MA (US); Stephen C. Cannon, Needham, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 09/717,743

(22) Filed: Nov. 21, 2000

Related U.S. Application Data

(63) Continuation-in-part of application No. 09/559,622, filed on Apr. 27, 2000, now Pat. No. 6,812,376.

(60) Provisional application No. 60/131,149, filed on Apr. 27, 1999.

(51) Int. Cl.
*C07H 21/02* (2006.01)
*C07H 21/04* (2006.01)

(52) U.S. Cl. .................. 536/23.5; 536/23.1; 536/23.4

(58) Field of Classification Search .............. 536/23.1, 536/23.5, 24.1
See application file for complete search history.

(56) References Cited

OTHER PUBLICATIONS

Ali et al., "Ionotropic and metabotropic activation of a neuronal chloride channel by serotonin and dopamine in the leech *Hirudo medicinalis*," *Journal of Physiology*, 509.1: 211-219, 1998.

De Montigny et al., "Tricyclic antidepressants: long-term treatment increases responsivity of rat forebrain neurons to serotonin," *Science*, 202:1303-1306, 1978.

Garner et al., "Serotonin activates Cl-channels in the apical membrane of rat choroid plexus epithelial cells," *Eur. J. Pharmacol.*, 239:31-37, 1993.

Hung et al., "Regulation of mouse choroid plexus apical $Cl^-$ and $K^+$ channels by serotonin," *Brain Res.*,, 617:285-295, 1993.

Koumenis et al., "Identification of Three Proteins in the Eye of Aplysia, Whose Synthesis Is Altered by Serotonin (5-HT)," *Journal of Biological Chemistry*, 270(24):14619-14627, 1995.

Lessmann et al., "Two kinetically distinct 5-hydroxytyptamine-activated Cl-conductances at Retzius P-cell synapses of the medicinal leech," *J. Neurosci.*, 15:1496-1505, 1995.*

Lessmann et al., "Development of Serotonin-Induced Ion Currents in Identified Embryonic Retzius Cells From the Medicinal Leech (*Hirudo medicinalis*)," *The J. of Neuroscience*, 11(3):800-809, 1991.

Liu et al., "High-Throughout Isolation of *Caenorhabditis elegans* Deletion Mutants," *Genome Research*, 9:859-887, 1999.

Madison et al., "Phorbol esters block a voltage-sensitive chloride current in hippocampal pyramidal cells," *Nature*, 321:695-697, 1986.

Munsch and Schlue, "Intracellular chloride activity and the effect of 5-hydroxytryptamine on the chloride conductance of leech Retzius neurons," *Eur. J. Neurosci.*, 5:1551-1557, 1993.

Parra et al., "How many subtypes of inhibitory cells in the hippocampus?," *Neuron*, 20:983-993, 1998.

Ranganathan and Horvitz, "mod-1 and mod-5, Two Genes Involved in the Serotonin-Mediated Experience-Dependent Modulation of Locomotion," 1998 East Coast *C. elegans* Meeting, May 12, 1998.

Ranganathan et al., "An Ionotropic Serotonin Receptor and a Serotonin Reuptake Transporter are Involved in Experience-Dependent Modulation of Behavior," 1999 International *C. elegans* Meeting, Mar. 17, 1999.

Scrogin et al., "Multiple receptor subtypes mediate the effects of serotonin on rat subfornical organ neurons," *Am. J. Physiol.*, 275(6 Pt 2):R2035-R2042, 1998.

Blakely et al., "Cloning and Expression of a Functional Serotonin Transporter from Rat Brain," *Nature* 354:66-70 (1991).

Choy and Thomas, "Fluoxetine-Resistant Mutants in *C. elegans* Define a Novel Family of Transmembrane Proteins," *Mol. Cell* 4:143-152 (1999).

Corey et al., "A Cocaine-Sensitive *Drosophila* Serotonin Transporter: Cloning, Expression, and Electrophysiological Characterization," *Proc. Natl. Acad. Sci. USA* 91:1188-1192 (1994).

Demchyshyn et al., "Cloning, Expression, and Localization of a Chloride-Facilitated, Cocaine-Sensitive Serotonin Transporter from *Drosophila melanogaster*," *Proc. Natl. Acad. Sci. USA* 91:5158-5162 (1994).

Desai et al., "A Genetic Pathway for the Development of the *Caenorhabditis elegans* HSN Motor Neurons," *Nature* 336: 638-646 (1988).

Hamdan et al., "Characterization of a Novel Serotonin Receptor from *Caenorhabditis elegans*: Cloning and Expression of Two Splice Variants," *Journal of Neurochemistry* 72:1372-1383 (1999).

Horvitz et al., "Serotonin and Octopamine in the Nematode *Caenorhabditis elegans*," *Science* 216:1012-1014 (1982).

(Continued)

Primary Examiner—Joseph Woitach
(74) Attorney, Agent, or Firm—Clark & Elbing, LLP

(57) ABSTRACT

Disclosed is a novel serotonin-gated anion channel that is permeable to chloride ions. Also disclosed are methods for the screening of therapeutics useful for treating serotonin-mediated cellular responses and conditions, as well as diagnostic methods for identifying such conditions.

2 Claims, 23 Drawing Sheets

OTHER PUBLICATIONS

Huang et al., "Alternative-Splicing of Serotonin Receptor Isoforms in the Pharynx and Muscle of the Parasitic Nematode, *Ascaris suum*," *Molecular and Biochemical Parasitology* 101:95-106 (1999).

Mendel et al., "Participation of the Protein $G_+$ in Multiple Aspects of Behavior in *C. elegans*," *Science* 267:1652-1655 (1995).

Olde and McCombie, "Molecular Cloning and Functional Expression of a Serotonin Receptor from *Caenorhabditis elegans*," *Journal of Molecular Neuroscience* 7:53-62 (1997).

Ramamoorthy et al., "Antidepressant- and Cocaine-Sensitive Human Serotonin Transporter: Molecular Cloning, Expression, and Chromosomal Localization," *Proc. Natl. Acad. Sci. USA* 90:2542-2546 (1993).

Ranganathan et al., "MOD-1 is a Serotonin-Gated Chloride Channel that Modulates Locomotory Behaviour in *C. elegans*," *Nature* 408:470-475 (2000).

Sawin, "Genetic and Cellular Analysis of Modulated Behaviors in *Caenorhabditis elegans*," Massachusetts Institute of Technology, (Ph.D. Thesis) (1996).

Sawin et al., "*C. elegans* Locomotory Rate Is Modulated by the Environment through a Dopaminergic Pathway, and by Experience through a Serotonergic Pathway," *Neuron* 26:619-631 (2000).

Ségalat et al., "Modulation of Serotonin-Controlled Behaviors by $G_+$ in *Caenorhabditis elegans*," *Science* 267:1648-1651 (1995).

Sze et al., "Food and Metabolic Signalling Defects in a *Caenorhabditis elegans* Serotonin-Synthesis Mutant," *Nature* 403: 560-564 (2000).

Trim et al., "Characterization of 5-HT Receptors in the Parasitic Nematode, *Ascaris suum*," *Parasitology* 122:207-217 (2001).

Weinshenker et al., "Genetic and Pharmacological Analysis of Neurotransmitters Controlling Egg Laying in *C. elegans*," *J. Neurosci.* 15:6975-6985 (1995).

Williams et al., "Identification of a Novel $5\text{-}HT_N$ (Nematoda) Receptor from *Ascaris suum* Muscle," *Comp. Biochem. Physiol.* 101C:469-474 (1992).

* cited by examiner

```
          10         20         30         40         50         60
  TCATGTTTCA CGGAACGACG AATTTATCCC GTCGTTTCTT CCTTTCCGTT TTAACTCATA 70         80         90        100        110        120
  TCTCTTCCTG GATCCTTCAG AGCTCTTGTC AATTCCTCAC GTTTTTTTTT GTTTTTTCGT 130        140        150        160        170        180
  CGTTTAATTG TGGAAACACA TATCCGTCCT CTTTGAAACA GCATCAGAAA ACTTTCTGCT 190        200        210        220        230        240
  CTCCGTGTCC TTCTACTTAC TCTGATTGCC TTAGTTAGTC ACATCGCAAG CAACAACTAA 250        260        270        280        290        300
  CTGCCAATGG GAGGAGCCAG TTGGAGCAGG GTGCGTGCTC GGTGCTCTTT TCAGAAGGTT 310        320        330        340        350        360
  TTCTCTTGTG CCAGCATGCT TTTTGAGGC TGTGTCATCA CAATGAACAT GTGTGAGTTC 370        380        390        400        410        420
  ATCCGTCTGG ATTATTCTTT TTCTTACGTC TTCTGAGTAC TTCATACTTT CCAAATTTTT 430        440        450        460        470        480
  CAACTGAACT TTTCTTCTTT TCTCATTGAA GTGGTTTGGT TTTGGTCGCG TGATCAACGG 490        500        510        520        530        540
  ATCCTACTTT TTTGAAACAA AATGTTTTTG AAGTTTCACA GACTGATTTC GGGGTTTTTT 550        560        570        580        590        600
  CAAAGAATAT ATTCCCTCTC GAGCAAGAGA AAATTCCAGA AAATAGTAGT TTTTTTCAAT 610        620        630        640        650        660
  TAGTCGTTTC ATTTGTACTA GCTAAAAAAC TTGCAACTTA TGGCTTTAAA ACATGTGTTG 670        680        690        700        710        720
  GCTTCATACA AAAACATTTA ACTAGTGTTT TTCCAGTTTT GTGTTCGTTT CATTTCTCA 730        740        750        760        770        780
  CCAAACTGAC AATAATTACT TTCTGTGAAC GTGTTTTGTA GGCAAGCTCC CGAATATTTT 790        800        810        820        830        840
  TTTCTCTTCT CACGTCTTGT TATTTCTCG ATTTTATTTT CTGAATCTGT GCGGTTTTCA 850        860        870        880        890        900
  ATCAATTTGA TTGCGATAAT TATTCTATCA GAAATATATT TTCAGAAATC CAAATACTCC 910        920        930        940        950        960
  AGGTGCCAAT GCGGTGAAAG AAAATTATGA AGTTTATTCC TGAAATCACA CTACTCTTGC 970        980        990       1000       1010       1020
  TTTTATTTGT ACACTCTACA CAGGTTAGTT GGTTGATTCT AGATCTCTTG CCTCCTAGCT 1030       1040       1050       1060       1070       1080
  TGCAAGGATA ATATAATTGA ATTGTTTTTG AGGAGTGCAA AGATTGAATA GTTTTCTATA 1090       1100       1110       1120       1130       1140
  TTTAGGCTAA AGGAAAACGA CGGAAATGTC CGGAGGGTGC GTGGTCGGAA GGAAAGATTA
```

Fig. 1

```
      1150       1160       1170       1180       1190       1200
TGAACACGAT CATGAGCAAC TACACGAAAA TGTTGCCCGA CGCGGAGGAC AGCGTACAAG 1210       1220       1230       1240       1250       1260
TTAATATTGA GATTCATGTA CAGGTTGGTA GACTCTATAA TTGCACACCA ATATGTGAAA 1270       1280       1290       1300       1310       1320
GTTTTCTTTA AAATTAAACT GCTGTAAATG ACTTTTGAAT AAGTTTATCA GATAGAAATT 1330       1340       1350       1360       1370       1380
GTCTGAACTT TTCGATTCAA ACTTTCCGAA CTTCAAAGCG GTTCCAAATT ACTCACTTCC 1390       1400       1410       1420       1430       1440
ATTTATCTCT TTGCTACAAT TTCTCCCACA AAGCCTTTTT CTTCATTTAA CGTTCTTTTT 1450       1460       1470       1480       1490       1500
TATGTCGTTG TTCTTACAAA CAATTTCGTC TCCTTGATGA ACTGCTTGAA CTGAGAATAG 1510       1520       1530       1540       1550       1560
TCACATGAGG ATAAATTTGA TGGAATGACA AGTTTTGTGC CCAGAAGGCA GTTTTGCACT 1570       1580       1590       1600       1610       1620
GAACTTGTTC AGTTGCAGAC ACATCTCAAA ACACAGAAGA TGAGTGGAAA ACTAGTGAGA 1630       1640       1650       1660       1670       1680
GACTGCCAAA AGTCGAAGGG ATAATGAAAA TTTGTTGCAA ATGAATTCTG CGAAGTTATG 1690       1700       1710       1720       1730       1740
TGAAAAATTA TTGGATTGGG AGTTGTGGGA GTGAAGAGAT GGGTCAAAAG CCATCAATCT 1750       1760       1770       1780       1790       1800
TGAATGCTTC GGTCAAAGAT TTGTTTCTCA TATGTTTACA ACACTGAAAA CAATCTATCC 1810       1820       1830       1840       1850       1860
TAGAAATGTT TGAACCACCC TCTAAAGTCC TTCCGTATAT TTTTTCATCT TTATACCGAC 1870       1880       1890       1900       1910       1920
CAGAATTCAA GAGTTGTTTG AAATAACTTC CTCTTTTTTG GAGAATATGT ACTCAGATTT 1930       1940       1950       1960       1970       1980
TTACATTCAA AATTTATATA TTTTCAAATA GAAAAAGTGC CAAGTACCAG AAACTTTTAT 1990       2000       2010       2020       2030       2040
CAAGTTGGCG GCACTTTGGA GAGTGAATTT GATGAAAAAG TGTTTGATAA GTTTGTCGGG 2050       2060       2070       2080       2090       2100
CAAACTGGTC CCCTGGGTGG GGAAATGGTG GCATTTTTGG AAACATTTTC ATAGTCGAAG 2110       2120       2130       2140       2150       2160
AAGTGGAACA AGAAAATTGG AAAATAGAGA TACATATGTA TATGAAAATA GAATTGAACA 2170       2180       2190       2200       2210       2220
GGAACTTATT TTTATTTTCA GGATATGGGA AGCTTGAATG AAATATCATC CGACTTTGAA 2230       2240       2250       2260       2270       2280
ATTGACATTT TATTCACTCA ACTGTGGCAT GACTCGGCAC TTTCTTTTGC TCATCTTCCG
```

Fig. 1 (cont'd)

```
       2290       2300       2310       2320       2330       2340
GCTTGTAAGC GGTAAGAAAT CTTTGTATTA GAAGGGAAAA ATATTTAAAT TAATGAAATT 2350       2360       2370       2380       2390       2400
TCAGAAATAT CACAATGGAA ACACGACTTT TACCTAAGAT TTGGTCTCCA AACACGTGTA 2410       2420       2430       2440       2450       2460
TGATTAATTC AAAACGAACA ACCGTCCATG CATCACCATC GGAAAATGTG ATGGTTATTC 2470       2480       2490       2500       2510       2520
TGTACGAGGT ATGATTTTTG ATTTTGTGAC GTCACAAACA GAGCATGTCT AAGGGCATGT 2530       2540       2550       2560       2570       2580
TGTAGCAAGA AAAAAACGGA TTCTTGTCTC TGTCGACGTT TCCTAAGTAT TGTGAATTAT 2590       2600       2610       2620       2630       2640
TTATAATACA TCACTCTAAT TACGTGAATA CTTACACCTT TAACTGGGTG AAGGATAAAA 2650       2660       2670       2680       2690       2700
TAGAGAAGGA GACGTTGAAA AAGCTCTTCG GTAGATTAAA GAGTCTAGAA TCGACATATG 2710       2720       2730       2740       2750       2760
TATTCATGTT TCTCGGTTCA GGGAAATAAG TGATTTGGC GAAAAAGAGT TAGACGACAT 2770       2780       2790       2800       2810       2820
TTTTTAGAAA ACTAAAACTA TATTCTCGAA CCCAAATCAG TCTAATGGTT TTCAGCAAAA 2830       2840       2850       2860       2870       2880
AGTATGAAAT ATACAATGTT TGTTTCAGAA TACCCAGTAC AAAATTTGAA GTTTTTCAGA 2890       2900       2910       2920       2930       2940
ATGGAACAGT CTGGATTAAC CATCGTCTTA GTGTCAAATC ACCTTGCAAT TTGGATCTGA 2950       2960       2970       2980       2990       3000
GACAGTTTCC TTTCGATACT CAAACTTGCA TATTAATCTT TGAATCCTAT AGTCATAACT 3010       3020       3030       3040       3050       3060
CAGAAGAAGT TGAACTTCAT TGGATGGAAG AAGCTGTCAC ATTAATGAAG CCAATTCAAC 3070       3080       3090       3100       3110       3120
TTCCTGACTT TGATATGGTT CATTATTCAA CTAAAAGGA AACTTTACTC TATCCAAACG 3130       3140       3150       3160       3170       3180
GGTACTGGGA TCAGCTTCAA GTTACTTTCA CTTTCAAACG ACGATATGGA TTCTATATTA 3190       3200       3210       3220       3230       3240
TTCAAGCCTA TGTTCCAACA TATCTTACAA TCATTGTATC TTGGGTTCA TTCTGCATGG 3250       3260       3270       3280       3290       3300
AACCAAAAGC TCTGCCGGCA AGAACAACTG TCGGAATCTC ATCTCTTCTA GCTCTTACTT 3310       3320       3330       3340       3350       3360
TCCAGTTTGG AAATATTTTG AAAAATCTTC CAAGGGTTTC ATATGTGAAA GGTTTGTTTT 3370       3380       3390       3400       3410       3420
TTTTCTTTTT CAAACAAATA AAAAAAAAGA TAAACAAATA TTTGTTTCAG CAATGGATGT
```

Fig. 1 (cont'd)

```
       3430       3440       3450       3460       3470       3480
GTGGATGCTT GGATGCATAT CATTTGTCTT CGGAACCATG GTAGAATTGG CATTTGTTTG 3490       3500       3510       3520       3530       3540
TTACATTTCC CGTTGTCAGA ACAGCGTAAG AAAGTGAGTT GGCATAAGAG TTTTCTCACG 3550       3560       3570       3580       3590       3600
TGGAGGGAAG TAATTAAATT TTGGGTGTCA TATGAAAATA TCAAAAACAA TATCAGGAAA 3610       3620       3630       3640       3650       3660
TTGAATTTCA CTATGATTTC GTAGTAAACA AATTACAGCG CGGAACGACG ACGGGAACGA 3670       3680       3690       3700       3710       3720
ATGAGAAATT CTCAGGTGTG GGCAAACGGA TCGTGTAGAA CTAGAAGCAA CGGGTATGCA 3730       3740       3750       3760       3770       3780
AACGGGGGAT CTGTAATCTC ACATTATCAT CCAACAAGCA ATGGAAATGG GAATAATAAT 3790       3800       3810       3820       3830       3840
CGACATGATA CACCTCAAGT TACTGGAAGG TTAGCAATCT CTATGATAGC ATTTATCAAT 3850       3860       3870       3880       3890       3900
TATTAAAGAA CTCTGGAATT AGTTTTTAAA GTATAAATAA ATCTCTATTT CTTGCGACCT 3910       3920       3930       3940       3950       3960
ACATTGAACT TAATAGTTAT GTTTTACAGA GGATCACTTC ATCGAAACGG GCCACCATCT 3970       3980       3990       4000       4010       4020
CCATTAAACC TTCAAATGAC TACATTTGAT TCGGAGATCC CTCTGACTTT TGATCAGGTG 4030       4040       4050       4060       4070       4080
AGTCTTACAT TGAGTTCAAA CTTTTTGAAT TTAAGCGTTC TATCTGATAA AGTTCTTCGG 4090       4100       4110       4120       4130       4140
TGGTTTTATA ATTTTTGATT CATAAACTTA CCCACTCCTT TCTCACTAAC ATTTTACCCT 4150       4160       4170       4180       4190       4200
GTTCAGCTGC CAGTTTCCAT GGAATCCGAT AGACCCCTGA TTGAAGAGGT AACTGTGAAA 4210       4220       4230       4240       4250       4260
GTAGTCAATT AATTCCCTGT GTTTCTACCC CACTCAATCC TTTTGTATTT TTGTTCAGT 4270       4280       4290       4300       4310       4320
CTATCCACTA TCAATGTCTT ATCACCTCTA GATACTGTTT AGAAGAAAAT ATTGTTCACA 4330       4340       4350       4360       4370       4380
GTTATGGAAA TCACATATAC TTTGTTCTGG AATTGTATAT GTATGCTTTG AAAAAGCACA 4390       4400       4410       4420       4430       4440
TTAGAATACT ACAAACATTA GTTTCCATCA GATTTTTGAT TTATCAAAAC CGTTATATTA 4450       4460       4470       4480       4490       4500
GACACTCTTA AGTTATCATA TTCTAATTTC CAAGAATGTT ATATTTGAA GAAGCCGGTG 4510       4520       4530       4540       4550       4560
ATTGTCAAAA AGATTGAAAA CTCCGAGTTT CTATATATGC GAAATTTTCA CTTCAGCCCA
```

Fig. 1 (cont'd)

```
           4570       4580       4590       4600       4610       4620
      CACACACACA CACACATTCA CGAAACTTTG TGTTGTTTAT GTTACTTATA TGTTATCTTT 4630       4640       4650       4660       4670       4680
      TCTGTCTGAT CATGGTTTTC GGACTGAAAT TGTGTTAATC GGAAGTTATA TGTGAGCCAC 4690       4700       4710       4720       4730       4740
      ATTGATTAAA CCTGTGAGAG ATGCCCATTT GTACTCATTT TACGACTGTC TCATGTCCAA 4750       4760       4770       4780       4790       4800
      ACACCATGTT TATTGTAATT ACCAGGCTAC TATTTGCAGA TGCGATCAAC ATCACCACCT 4810       4820       4830       4840       4850       4860
      CCACCATCTG GATGTCTGGC CAGATTCCAT CCGGAAGCAG TGGACAAATT CTCCATTGTA 4870       4880       4890       4900       4910       4920
      GCTTTTCCAT TGGCATTTAC AATGTTTAAT GTTAGTTAAT CCACAGTTAA AAATTCCCAT 4930       4940       4950       4960       4970       4980
      AATCATAAAT ATCTCGACTT TTCAGCTTGT CTACTGGTGG CACTATTTGT CTCAAACTTT 4490       5000       5010       5020       5030       5040
      CGATCAAAAC TATCAGTGAT TGAAGTTTAT CCCTTTTAAT TCCAATAATT CACAGTTGCC 5050       5060       5070       5080       5090       5100
      GGTATCTACC TCCATTCTTT TCCGATGATT CGCAGTTTTT CACAGGGTTC AAATGTATCT 5110       5120       5130       5140       5150       5160
      CGTTCAATCT TTTTATGGTT ATTTCTCTTG AATGTCCATT TTAATATTTA TAGAACACTT 5170       5180       5190       5200       5210       5220
      TTATGTACAT TGTGTTGGTA TTCAATTCGA AAAACAATGA AATTTATTTC TAAATAACTG 5230       5240       5250       5260       5270       5280
      CGTTTCTGGG GTTTCTATCA GCACTTACTA GCTGACAAAA ACTTTTCCGT ATTCGGAATT 5290       5300       5310       5320       5330       5340
      AGATTTTTAT GCAAGCAATG TTTCATTTTT ACACAGTATA GTATTTATTC TTACTTTTGA 5350       5360       5370       5380       5390       5400
      TTATATTGCT CGCACCCTAA ATGACAGGTA TTAGAAATTA ACCGCTTTTC AGAGTATTTT 5410       5420       5430       5440       5450       5460
      TAATCTTCTT AGTACTAGTT TAGTTCTTTA AATAAGAAAC CATCTAGTTT TTCATTATCA 5470       5480       5490       5500       5510       5520
      CTCAACTTCA GTCGGACAAA TTTTAAATTT TTTACTCGAT AAAAAAATTT TATAATTCAG 5530       5540       5550
      ACAAATTATG TCTTCTCATT TTTGATCGCT
```

Fig. 1 (cont'd)

```
         10         20         30         40         50
ATGAAGTTTA TTCCTGAAAT CACACTACTC TTGCTTTTAT TTGTACACTC 60         70         80         90        100
TACACAGGCT AAAGGAAAAC GACGGAAATG TCCGGAGGGT GCGTGGTCGG 110        120        130        140        150
AAGGAAAGAT TATGAACACG ATCATGAGCA ACTACACGAA AATGTTGCCC 160        170        180        190        200
GACGCGGAGG ACAGCGTACA AGTTAATATT GAGATTCATG TACAGGATAT 210        220        230        240        250
GGGAAGCTTG AATGAAATAT CATCCGACTT TGAAATTGAC ATTTTATTCA 260        270        280        290        300
CTCAACTGTG GCATGACTCG GCACTTTCTT TTGCTCATCT TCCGGCTTGT 310        320        330        340        350
AAGCGAAATA TCACAATGGA AACACGACTT TTACCTAAGA TTTGGTCTCC 360        370        380        390        400
AAACACGTGT ATGATTAATT CAAAACGAAC AACCGTCCAT GCATCACCAT 410        420        430        440        450
CGGAAAATGT GATGGTTATT CTGTACGAGA ATGGAACAGT CTGGATTAAC 460        470        480        490        500
CATCGTCTTA GTGTCAAATC ACCTTGCAAT TTGGATCTGC GACAGTTTCC 510        520        530        540        550
TTTCGATACT CAAACTTGCA TATTAATCTT TGAATCCTAT AGTCATAACT 560        570        580        590        600
CAGAAGAAGT TGAACTTCAT TGGATGGAAG AAGCTGTCAC ATTAATGAAG 610        620        630        640        650
CCAATTCAAC TTCCTGACTT TGATATGGTT CATTATTCAA CTAAAAAGGA 660        670        680        690        700
AACTTTACTC TATCCAAACG GGTACTGGGA TCAGCTTCAA GTTACTTTCA 710        720        730        740        750
CTTTCAAACG ACGATATGGA TTCTATATTA TTCAAGCCTA TGTTCCAACA 760        770        780        790        800
TATCTTACAA TCATTGTATC TTGGGTTTCA TTCTGCATGG AACCAAAAGC 810        820        830        840        850
TCTGCCGGCA AGAACAACTG TCGGAATCTC ATCTCTTCTA GCTCTTACTT 860        870        880        890        900
TCCAGTTTGG AAATATTTTG AAAAATCTTC CAAGGGTTTC ATATGTGAAA 910        920        930        940        950
GCAATGGATG TGTGGATGCT TGGATGCATA TCATTTGTCT TCGGAACCAT
```

Fig. 2

```
           960        970        980        990       1000
    GGTAGAATTG GCATTTGTTT GTTACATTTC CCGTTGTCAG AACAGCGTAA 1010       1020       1030       1040       1050
    GAAACGCGGA ACGACGACGG GAACGAATGA GAAATTCTCA GGTGTGGGCA 1060       1070       1080       1090       1100
    AACGGATCGT GTAGAACTAG AAGCAACGGG TATGCAAACG GGGGATCTGT 1110       1120       1130       1140       1150
    AATCTCACAT TATCATCCAA CAAGCAATGG AAATGGGAAT AATAATCGAC 1160       1170       1180       1190       1200
    ATGATACACC TCAAGTTACT GGAAGAGGAT CACTTCATCG AAACGGGCCA 1210       1220       1230       1240       1250
    CCATCTCCAT TAAACCTTCA AATGACTACA TTTGATTCGG AGATCCCTCT 1260       1270       1280       1290       1300
    GACTTTTGAT CAGCTGCCAG TTTCCATGGA ATCCGATAGA CCCCTGATTG 1310       1320       1330       1340       1350
    AAGAGATGCG ATCAACATCA CCACCTCCAC CATCTGGATG TCTGGCCAGA 1360       1370       1380       1390       1400
    TTCCATCCGG AAGCAGTGGA CAAATTCTCC ATTGTAGCTT TTCCATTGGC 1410       1420       1430       1440       1450
    ATTTACAATG TTTAATCTTG TCTACTGGTG GCACTATTTG TCTCAAACTT 1460       1470
    TCGATCAAAA CTATCAGTGA
```

Fig. 2 (cont'd)

```
          10          20          30          40          50
   MKFIPEITLL  LLLFVHSTQA  KGKRRKCPEG  AWSEGKIMNT  IMSNYTKMLP 60          70          80          90         100
   DAEDSVQVNI  EIHVQDMGSL  NEISSDFEID  ILFTQLWHDS  ALSFAHLPAC 110         120         130         140         150
   KRNITMETRL  LPKIWSPNTC  MINSKRTTVH  ASPSENVMVI  LYENGTVWIN 160         170         180         190         200
   HRLSVKSPCN  LDLRQFPFDT  QTCILIFESY  SHNSEEVELH  WMEEAVTLMK 210         220         230         240         250
   PIQLPDFDMV  HYSTKKETLL  YPNGYWDQLQ  VTFTFKRRYG  FYIIQAYVPT 260         270         280         290         300
   YLTIIVSWVS  FCMEPKALPA  RTTVGISSLL  ALTFQFGNIL  KNLPRVSYVK 310         320         330         340         350
   AMDVWMLGCI  SFVFGTMVEL  AFVCYISRCQ  NSVRNAERRR  ERMRNSQVWA 360         370         380         390         400
   NGSCRTRSNG  YANGGSVISH  YHPTSNGNGN  NNRHDTPQVT  GRGSLHRNGP 410         420         430         440         450
   PSPLNLQMTT  FDSEIPLTFD  QLPVSMESDR  PLIEEMRSTS  PPPPSGCLAR 460         470         480
   FHPEAVDKFS  IVAFPLAFTM  FNLVYWWHYL  SQTFDQNYQ
```

Fig. 3

```
         10          20         30          40         50          60
TCATGTTTCA CGGAACGACG AATTTATCCC GTCGTTTCTT CCTTTCCGTT TTAACTCATA 70          80         90         100        110         120
TCTCTTCCTG GATCCTTCAG AGCTCTTGTC AATTCCTCAC GTTTTTTTTT GTTTTTTCGT 130         140        150         160        170         180
CGTTTAATTG TGGAAACACA TATCCGTCCT CTTTGAAACA GCATCAGAAA ACTTTCTGCT 190         200        210         220        230         240
CTCCGTGTCC TTCTACTTAC TCTGATTGCC TTAGTTAGTC ACATCGCAAG CAACAACTAA 250         260        270         280        290         300
CTGCCAATGG GAGGAGCCAG TTGGAGCAGG GTGCGTGCTC GGTGCTCTTT TCAGAAGGTT 310         320        330         340        350         360
TTCTCTTGTG CCAGCATGCT TTTTGAGGC TGTGTCATCA CAATGAACAT GTGTGAGTTC 370         380        390         400        410         420
ATCCGTCTGG ATTATTCTTT TCTTACGTC TTCTGAGTAC TTCATACTTT CCAAATTTTT 430         440        450         460        470         480
CAACTGAACT TTTCTTCTTT TCTCATTGAA GTGGTTTGGT TTTGGTCGCG TGATCAACGG 490         500        510         520        530         540
ATCCTACTTT TTTGAAACAA AATGTTTTTG AAGTTTCACA GACTGATTTC GGGGTTTTTT 550         560        570         580        590         600
CAAAGAATAT ATTCCCTCTC GAGCAAGAGA AAATTCCAGA AAATAGTAGT TTTTTTCAAT 610         620        630         640        650         660
TAGTCGTTTC ATTTGTACTA GCTAAAAAAC TTGCAACTTA TGGCTTTAAA ACATGTGTTG 670         680        690         700        710         720
GCTTCATACA AAAACATTTA ACTAGTGTTT TTCCAGTTTT GTGTTCGTTT CATTTCTCA 730         740        750         760        770         780
CCAAACTGAC AATAATTACT TTCTGTGAAC GTGTTTTGTA GGCAAGCTCC CGAATATTTT 790         800        810         820        830         840
TTTCTCTTCT CACGTCTTGT TATTTCTCG ATTTTATTTT CTGAATCTGT GCGGTTTTCA 850         860        870         880        890         900
ATCAATTTGA TTGCGATAAT TATTCTATCA GAAATATATT TTCAGAAATC CAAATACTCC 910         920        930         940        950         960
AGGTGCCAAT GCGGTGAAAG AAAATTATGA AGTTTATTCC TGAAATCACA CTACTCTTGC 970         980        990        1000       1010        1020
TTTTATTTGT ACACTCTACA CAGGTTAGTT TCTCTTGAAT GTCCATTTTA ATATTTATAG 1030        1040       1050        1060       1070        1080
AACACTTTTA TGTACATTGT GTTGGTATTC AATTCGAAAA ACAATGAAAT TTATTTCTAA 1090        1100       1110        1120       1130        1140
ATAACTGCGT TTCTGGGGTT TCTATCAGCA CTTACTAGCT GACAAAAACT TTTCCGTATT
```

Fig. 6

```
        1150       1160       1170       1180       1190       1200
    CGGAATTAGA TTTTTATGCA AGCAATGTTT CATTTTTACA CAGTATAGTA TTTATTCTTA 1210       1220       1230       1240       1250       1260
    CTTTTGATTA TATTGCTCGC ACCCTAAATG ACAGGTATTA GAAATTAACC GCTTTTCAGA 1270       1280       1290       1300       1310       1320
    GTATTTTAA TCTTCTTAGT ACTAGTTTAG TTCTTTAAAT AAGAAACCAT CTAGTTTTTC 1330       1340       1350       1360       1370       1380
    ATTATCACTC AACTTCAGTC GGACAAATTT TAAATTTTTT ACTCGATAAA AAAATTTAT 1390       1400       1410
    AATTCAGACA AATTATGTCT TCTCATTTTT GATCGCT
```

Fig. 6 (cont'd)

```
          10         20         30         40         50         60
TCATGTTTCA CGGAACGACG AATTTATCCC GTCGTTTCTT CCTTTCCGTT TTAACTCATA 70         80         90        100        110        120
TCTCTTCCTG GATCCTTCAG AGCTCTTGTC AATTCCTCAC GTTTTTTTTT GTTTTTTCGT 130        140        150        160        170        180
CGTTTAATTG TGGAAACACA TATCCGTCCT CTTTGAAACA GCATCAGAAA ACTTTCTGCT 190        200        210        220        230        240
CTCCGTGTCC TTCTACTTAC TCTGATTGCC TTAGTTAGTC ACATCGCAAG CAACAACTAA 250        260        270        280        290        300
CTGCCAATGG GAGGAGCCAG TTGGAGCAGG GTGCGTGCTC GGTGCTCTTT TCAGAAGGTT 310        320        330        340        350        360
TTCTCTTGTG CCAGCATGCT TTTTGAGGC TGTGTCATCA CAATGAACAT GTGTGAGTTC 370        380        390        400        410        420
ATCCGTCTGG ATTATTCTTT TTCTTACGTC TTCTGAGTAC TTCATACTTT CCAAATTTTT 430        440        450        460        470        480
CAACTGAACT TTTCTTCTTT TCTCATTGAA GTGGTTTGGT TTTGGTCGCG TGATCAACGG 490        500        510        520        530        540
ATCCTACTTT TTTGAAACAA AATGTTTTTG AAGTTTCACA GACTGATTTC GGGGTTTTTT 550        560        570        580        590        600
CAAAGAATAT ATTCCCTCTC GAGCAAGAGA AAATTCCAGA AAATAGTAGT TTTTTTCAAT 610        620        630        640        650        660
TAGTCGTTTC ATTTGTACTA GCTAAAAAAC TTGCAACTTA TGGCTTTAAA ACATGTGTTG 670        680        690        700        710        720
GCTTCATACA AAAACATTTA ACTAGTGTTT TTCCAGTTTT GTGTTCGTTT CATTTCTCA 730        740        750        760        770        780
CCAAACTGAC AATAATTACT TTCTGTGAAC GTGTTTTGTA GGCAAGCTCC CGAATATTTT 790        800        810        820        830        840
TTTCTCTTCT CACGTCTTGT TATTTTCTCG ATTTTATTTT CTGAATCTGT GCGGTTTTCA 850        860        870        880        890        900
ATCAATTTGA TTGCGATAAT TATTCTATCA GAAATATATT TTCAGAAATC CAAATACTCC 910        920        930        940        950        960
AGGTGCCAAT GCGGTGAAAG AAAATTATGA AGTTTATTCC TGAAATCACA CTACTCTTGC 970        980        990       1000       1010       1020
TTTTATTTGT ACACTCTACA CAGGTTAGTT GGTTGATTCT AGATCTCTTG CCTCCTAGCT 1030       1040       1050       1060       1070       1080
TGCAAGGATA ATATAATTGA ATTGTTTTTG AGGAGTGCAA AGATTGAATA GTTTTCTATA 1090       1100       1110       1120       1130       1140
TTTAGGCTAA AGGAAAACGA CGGAAATGTC CGGAGGGTGC GTGGTCGGAA GGAAAGATTA
```

Fig. 7

```
            1150       1160       1170       1180       1190       1200
        TGAACACGAT CATGAGCAAC TACACGAAAA TGTTGCCCGA CGCGGAGGAC AGCGTACAAG 1210       1220       1230       1240       1250       1260
        TTAATATTGA GATTCATGTA CAGGTTGGTA GACTCTATAA TTGCACACCA ATATGTGAAA 1270       1280       1290       1300       1310       1320
        GTTTTCTTTA AAATTAAACT GCTGTAAATG ACTTTTGAAT AAGTTTATCA GATAGAAATT 1330       1340       1350       1360       1370       1380
        GTCTGAACTT TTCGATTCAA ACTTTCCGAA CTTCAAAGCG GTTCCAAATT ACTCACTTCC 1390       1400       1410       1420       1430       1440
        ATTTATCTCT TTGCTACAAT TTCTCCCACA AAGCCTTTTT CTTCATTTAA CGTTCTTTTT 1450       1460       1470       1480       1490       1500
        TATGTCGTTG TTCTTACAAA CAATTTCGTC TCCTTGATGA ACTGCTTGAA CTGAGAATAG 1510       1520       1530       1540       1550       1560
        TCACATGAGG ATAAATTTGA TGGAATGACA AGTTTTGTGC CCAGAAGGCA GTTTTGCACT 1570       1580       1590       1600       1610       1620
        GAACTTGTTC AGTTGCAGAC ACATCTCAAA ACACAGAAGA TGAGTGGAAA ACTAGTGAGA 1630       1640       1650       1660       1670       1680
        GACTGCCAAA AGTCGAAGGG ATAATGAAAA TTTGTTGCAA ATGAATTCTG CGAAGTTATG 1690       1700       1710       1720       1730       1740
        TGAAAAATTA TTGGATTGGG AGTTGTGGGA GTGAAGAGAT GGGTCAAAAG CCATCAATCT 1750       1760       1770       1780       1790       1800
        TGAATGCTTC GGTCAAAGAT TTGTTTCTCA TATGTTTACA ACACTGAAAA CAATCTATCC 1810       1820       1830       1840       1850       1860
        TAGAAATGTT TGAACCACCC TCTAAAGTCC TTCCGTATAT TTTTCATCT TTATACCGAC 1870       1880       1890       1900       1910       1920
        CAGAATTCAA GAGTTGTTTG AAATAACTTC CTCTTTTTTG GAGAATATGT ACTCAGATTT 1930       1940       1950       1960       1970       1980
        TTACATTCAA AATTTATATA TTTTCAAATA GAAAAAGTGC CAAGTACCAG AAACTTTTAT 1990       2000       2010       2020       2030       2040
        CAAGTTGGCG GCACTTTGGA GAGTGAATTT GATGAAAAAG TGTTTGATAA GTTTGTCGGG 2050       2060       2070       2080       2090       2100
        CAAACTGGTC CCCTGGGTGG GGAAATGGTG GCATTTTGG AAACATTTTC ATAGTCGAAG 2110       2120       2130       2140       2150       2160
        AAGTGGAACA AGAAAATTGG AAAATAGAGA TACATATGTA TATGAAAATA GAATTGAACA 2170       2180       2190       2200       2210       2220
        GGAACTTATT TTTATTTTCA GGATATGGGA AGCTTGAATG AAATATCATC CGACTTTGAA 2230       2240       2250       2260       2270       2280
        ATTGACATTT TATTCACTCA ACTGTGGCAT GACTCGGCAC TTTCTTTTGC TCATCTTCCG
```

Fig. 7 (cont'd)

```
      2290       2300       2310       2320       2330       2340
GCTTGTAAGC GGTAAGAAAT CTTTGTATTA GAAGGGAAAA ATATTTAAAT TAATGAAATT 2350       2360       2370       2380       2390       2400
TCAGAAATAT CACAATGGAA ACACGACTTT TACCTAAGAT TTGGTCTCCA AACACGTGTA 2410       2420       2430       2440       2450       2460
TGATTAATTC AAAACGAACA ACCGTCCATG CATCACCATC GGAAAATGTG ATGGTTATTC 2470       2480       2490       2500       2510       2520
TGTACGAGGT ATGATTTTTG ATTTGTGAC GTCACAAACA GAGCATGTCT AAGGGCATGT 2530       2540       2550       2560       2570       2580
TGTAGCAAGA AAAAAACGGA TTCTTGTCTC TGTCGACGTT TCCTAAGTAT TGTGAATTAT 2590       2600       2610       2620       2630       2640
TTATAATACA TCACTCTAAT TACGTGAATA CTTACACCTT TAACTGGGTG AAGGATAAAA 2650       2660       2670       2680       2690       2700
TAGAGAAGGA GACGTTGAAA AAGCTCTTCG GTAGATTAAA GAGTCTAGAA TCGACATATG 2710       2720       2730       2740       2750       2760
TATTCATGTT TCTCGGTTCA GGGAAATAAG TGATTTTGGC GAAAAAGAGT TAGACGACAT 2770       2780       2790       2800       2810       2820
TTTTTAGAAA ACTAAAACTA TATTCTCGAA CCCAAATCAG TCTAATGGTT TTCAGCAAAA 2830       2840       2850       2860       2870       2880
AGTATGAAAT ATACAATGTT TGTTTCAGAA TACCCAGTAC AAAATTTGAA GTTTTTCAGA 2890       2900       2910       2920       2930       2940
ATGGAACAGT CTGGATTAAC CATCGTCTTA GTGTCAAATC ACCTTGCAAT TTGGATCTGC 2950       2960       2970       2980       2990       3000
GACAGTTTCC TTTCGATACT CAAACTTGCA TATTAATCTT TGAATCCTAT AGTCATAACT 3010       3020       3030       3040       3050       3060
CAGAAGAAGT TGAACTTCAT TGGATGGAAG AAGCTGTCAC ATTAATGAAG CCAATTCAAC 3070       3080       3090       3100       3110       3120
TTCCTGACTT TGATATGGTT CATTATTCAA CTAAAAGGA AACTTTACTC TATCCAAACG 3130       3140       3150       3160       3170       3180
GGTACTGGGA TCAGCTTCAA GTTACTTTCA CTTTCAAACG ACGATATGGA TTCTATATTA 3190       3200       3210       3220       3230       3240
TTCAAGCCTA TGTTCCAACA TATCTTACAA TCATTGTATC TTGGGTTTCA TTCTGCATGG 3250       3260       3270       3280       3290       3300
AACCAAAAGC TCTGCCGGCA AGAACAACTG TCGGAATCTC ATCTCTTCTA GTTCTTACTT 3310       3320       3330       3340       3350       3360
TCCAGTTTGG AAATATTTTG AAAAATCTTC CAAGGGTTTC ATATGTGAAA GGTTTGTTTT 3370       3380       3390       3400       3410       3420
TTTTCTTTTT CAAACAAATA AAAAAAAAGA TAAACAAATA TTTGTTTCAG CAATGGATGT
```

Fig. 7 (cont'd)

```
       3430       3440       3450       3460       3470       3480
GTGGATGCTT GGATGCATAT CATTTGTCTT CGGAACCATG GTAGAATTGG CATTTGTTTG
       3490       3500       3510       3520       3530       3540
TTACATTTCC CGTTGTCAGA ACAGCGTAAG AAAGTGAGTT GGCATAAGAG TTTTCTCACG
       3550       3560       3570       3580       3590       3600
TGGAGGGAAG TAATTAAATT TTGGGTGTCA TATGAAAATA TCAAAAACAA TATCAGGAAA
       3610       3620       3630       3640       3650       3660
TTGAATTTCA CTATGATTTC GTAGTAAACA AATTACAGCG CGGAACGACG ACGGGAACGA
       3670       3680       3690       3700       3710       3720
ATGAGAAATT CTCAGGTGTG GGCAAACGGA TCGTGTAGAA CTAGAAGCAA CGGGTATGCA
       3730       3740       3750       3760       3770       3780
AACGGGGGAT CTGTAATCTC ACATTATCAT CCAACAAGCA ATGGAAATGG GAATAATAAT
       3790       3800       3810       3820       3830       3840
CGACATGATA CACCTCAAGT TACTGGAAGG TTAGCAATCT CTATGATAGC ATTTATCAAT
       3850       3860       3870       3880       3890       3900
TATTAAAGAA CTCTGGAATT AGTTTTTAAA GTATAAATAA ATCTCTATTT CTTGCGACCT
       3910       3920       3930       3940       3950       3960
ACATTGAACT TAATAGTTAT GTTTTACAGA GGATCACTTC ATCGAAACGG GCCACCATCT
       3970       3980       3990       4000       4010       4020
CCATTAAACC TTCAAATGAC TACATTTGAT TCGGAGATCC CTCTGACTTT TGATCAGGTG
       4030       4040       4050       4060       4070       4080
AGTCTTACAT TGAGTTCAAA CTTTTTGAAT TTAAGCGTTC TATCTGATAA AGTTCTTCGG
       4090       4100       4110       4120       4130       4140
TGGTTTTATA ATTTTTGATT CATAAACTTA CCCACTCCTT TCTCACTAAC ATTTTACCCT
       4150       4160       4170       4180       4190       4200
GTTCAGCTGC CAGTTTCCAT GGAATCCGAT AGACCCCTGA TTGAAGAGGT AACTGTGAAA
       4210       4220       4230       4240       4250       4260
GTAGTCAATT AATTCCCTGT GTTTCTACCC CACTCAATCC TTTTGTATTT TTTGTTCAGT
       4270       4280       4290       4300       4310       4320
CTATCCACTA TCAATGTCTT ATCACCTCTA GATACTGTTT AGAAGAAAAT ATTGTTCACA
       4330       4340       4350       4360       4370       4380
GTTATGGAAA TCACATATAC TTTGTTCTGG AATTGTATAT GTATGCTTTG AAAAAGCACA
       4390       4400       4410       4420       4430       4440
TTAGAATACT ACAAACATTA GTTTCCATCA GATTTTTGAT TTATCAAAAC CGTTATATTA
       4450       4460       4470       4480       4490       4500
GACACTCTTA AGTTATCATA TTCTAATTTC CAAGAATGTT ATATTTTGAA GAAGCCGGTG
       4510       4520       4530       4540       4550       4560
ATTGTCAAAA AGATTGAAAA CTCCGAGTTT CTATATATGC GAAATTTTCA CTTCAGCCCA
```

Fig. 7 (cont'd)

```
       4570       4580       4590       4600       4610       4620
  CACACACACA CACACATTCA CGAAACTTTG TGTTGTTTAT GTTACTTATA TGTTATCTTT 4630       4640       4650       4660       4670       4680
  TCTGTCTGAT CATGGTTTTC GGACTGAAAT TGTGTTAATC GGAAGTTATA TGTGAGCCAC 4690       4700       4710       4720       4730       4740
  ATTGATTAAA CCTGTGAGAG ATGCCCATTT GTACTCATTT TACGACTGTC TCATGTCCAA 4750       4760       4770       4780       4790       4800
  ACACCATGTT TATTGTAATT ACCAGGCTAC TATTTGCAGA TGCGATCAAC ATCACCACCT 4810       4820       4830       4840       4850       4860
  CCACCATCTG GATGTCTGGC CAGATTCCAT CCGGAAGCAG TGGACAAATT CTCCATTGTA 4870       4880       4890       4900       4910       4920
  GCTTTTCCAT TGGCATTTAC AATGTTTAAT GTTAGTTAAT CCACAGTTAA AAATTCCCAT 4930       4940       4950       4960       4970       4980
  AATCATAAAT ATCTCGACTT TTCAGCTTGT CTACTGGTGG CACTATTTGT CTCAAACTTT 4990       5000       5010       5020       5030       5040
  CGATCAAAAC TATCAGTGAT TGAAGTTTAT CCCTTTTAAT TCCAATAATT CACAGTTGCC 5050       5060       5070       5080       5090       5100
  GGTATCTACC TCCATTCTTT TCCGATGATT CGCAGTTTTT CACAGGGTTC AAATGTATCT 5110       5120       5130       5140       5150       5160
  CGTTCAATCT TTTTATGGTT ATTTCTCTTG AATGTCCATT TTAATATTTA TAGAACACTT 5170       5180       5190       5200       5210       5220
  TTATGTACAT TGTGTTGGTA TTCAATTCGA AAAACAATGA AATTTATTTC TAAATAACTG 5230       5240       5250       5260       5270       5280
  CGTTTCTGGG GTTTCTATCA GCACTTACTA GCTGACAAAA ACTTTTCCGT ATTCGGAATT 5290       5300       5310       5320       5330       5340
  AGATTTTTAT GCAAGCAATG TTTCATTTTT ACACAGTATA GTATTTATTC TTACTTTTGA 5350       5360       5370       5380       5390       5400
  TTATATTGCT CGCACCCTAA ATGACAGGTA TTAGAAATTA ACCGCTTTTC AGAGTATTTT 5410       5420       5430       5440       5450       5460
  TAATCTTCTT AGTACTAGTT TAGTTCTTTA AATAAGAAAC CATCTAGTTT TTCATTATCA 5470       5480       5490       5500       5510       5520
  CTCAACTTCA GTCGGACAAA TTTTAAATTT TTTACTCGAT AAAAAAATTT TATAATTCAG 5530       5540       5550
  ACAAATTATG TCTTCTCATT TTTGATCGCT
```

Fig. 7 (cont'd)

```
          10         20         30         40         50         60
ATGAAGTTTA TTCCTGAAAT CACACTACTC TTGCTTTTAT TTGTACACTC TACACAGGCT 70         80         90        100        110        120
AAAGGAAAAC GACGGAAATG TCCGGAGGGT GCGTGGTCGG AAGGAAAGAT TATGAACACG 130        140        150        160        170        180
ATCATGAGCA ACTACACGAA AATGTTGCCC GACGCGGAGG ACAGCGTACA AGTTAATATT 190        200        210        220        230        240
GAGATTCATG TACAGGATAT GGGAAGCTTG AATGAAATAT CATCCGACTT TGAAATTGAC 250        260        270        280        290        300
ATTTTATTCA CTCAACTGTG GCATGACTCG GCACTTTCTT TTGCTCATCT TCCGGCTTGT 310        320        330        340        350        360
AAGCGAAATA TCACAATGGA AACACGACTT TTACCTAAGA TTTGGTCTCC AAACACGTGT 370        380        390        400        410        420
ATGATTAATT CAAAACGAAC AACCGTCCAT GCATCACCAT CGGAAAATGT GATGGTTATT 430        440        450        460        470        480
CTGTACGAGA ATGGAACAGT CTGGATTAAC CATCGTCTTA GTGTCAAATC ACCTTGCAAT 490        500        510        520        530        540
TTGGATCTGC GACAGTTTCC TTTCGATACT CAAACTTGCA TATTAATCTT TGAATCCTAT 550        560        570        580        590        600
AGTCATAACT CAGAAGAAGT TGAACTTCAT TGGATGGAAG AAGCTGTCAC ATTAATGAAG 610        620        630        640        650        660
CCAATTCAAC TTCCTGACTT TGATATGGTT CATTATTCAA CTAAAAAGGA AACTTTACTC 670        680        690        700        710        720
TATCCAAACG GGTACTGGGA TCAGCTTCAA GTTACTTTCA CTTTCAAACG ACGATATGGA 730        740        750        760        770        780
TTCTATATTA TTCAAGCCTA TGTTCCAACA TATCTTACAA TCATTGTATC TTGGGTTTCA 790        800        810        820        830        840
TTCTGCATGG AACCAAAAGC TCTGCCGGCA AGAACAACTG TCGGAATCTC ATCTCTTCTA 850        860        870        880        890        900
GTTCTTACTT TCCAGTTTGG AAATATTTTG AAAAATCTTC CAAGGGTTTC ATATGTGAAA 910        920        930        940        950        960
GCAATGGATG TGTGGATGCT TGGATGCATA TCATTTGTCT TCGGAACCAT GGTAGAATTG 970        980        990       1000       1010       1020
GCATTTGTTT GTTACATTTC CCGTTGTCAG AACAGCGTAA GAAACGCGGA ACGACGACGG 1030       1040       1050       1060       1070       1080
GAACGAATGA GAAATTCTCA GGTGTGGGCA AACGGATCGT GTAGAACTAG AAGCAACGGG 1090       1100       1110       1120       1130       1140
TATGCAAACG GGGGATCTGT AATCTCACAT TATCATCCAA CAAGCAATGG AAATGGGAAT
```

Fig. 8

```
          1150       1160       1170       1180       1190       1200
     AATAATCGAC ATGATACACC TCAAGTTACT GGAAGAGGAT CACTTCATCG AAACGGGCCA 1210       1220       1230       1240       1250       1260
     CCATCTCCAT TAAACCTTCA AATGACTACA TTTGATTCGG AGATCCCTCT GACTTTTGAT 1270       1280       1290       1300       1310       1320
     CAGCTGCCAG TTTCCATGGA ATCCGATAGA CCCCTGATTG AAGAGATGCG ATCAACATCA 1330       1340       1350       1360       1370       1380
     CCACCTCCAC CATCTGGATG TCTGGCCAGA TTCCATCCGG AAGCAGTGGA CAAATTCTCC 1390       1400       1410       1420       1430       1440
     ATTGTAGCTT TTCCATTGGC ATTTACAATG TTTAATCTTG TCTACTGGTG GCACTATTTG 1450       1460       1470
     TCTCAAACTT TCGATCAAAA CTATCAGTGA
```

Fig. 8 (cont'd)

Oocyte injected with rat cortex poly(A)+ RNA.
Membrane potential -70 mV. 1 μM 5-HT applied (bar)
Oocyte was pretreated with 0.2 mM BAPTA-AM for 2 hours.
The bath solution contained 2 mM $Co^{2+}$ to block 5-HT3a responses.

SEQUENCE LISTING

<160> NUMBER OF SEQ ID NOS: 6

<210> SEQ ID NO 1
<211> LENGTH: 5550
<212> TYPE: DNA
<213> ORGANISM: Caenorhabditis elegans

<400> SEQUENCE: 1

```
tcatgtttca cggaacgacg aatttatccc gtcgtttctt cctttccgtt ttaactcata      60
tctcttcctg gatccttcag agctcttgtc aattcctcac gttttttttt gttttttcgt     120
cgtttaattg tggaaacaca tatccgtcct ctttgaaaca gcatcagaaa actttctgct     180
ctccgtgtcc ttctacttac tctgattgcc ttagttagtc acatcgcaag caacaactaa     240
ctgccaatgg gaggagccag ttggagcagg gtgcgtgctc ggtgctcttt tcagaaggtt     300
ttctcttgtg ccagcatgct tttttgaggc tgtgtcatca caatgaacat gtgtgagttc     360
atccgtctgg attattcttt ttcttacgtc ttctgagtac ttcatacttt ccaaattttt     420
caactgaact tttcttcttt tctcattgaa gtggtttggt tttggtcgcg tgatcaacgg     480
atcctacttt tttgaaacaa aatgtttttg aagtttcaca gactgatttc ggggtttttt     540
caaagaatat attccctctc gagcaagaga aaattccaga aaatagtagt ttttttcaat     600
tagtcgtttc atttgtacta gctaaaaaac ttgcaactta tggctttaaa acatgtgttg     660
gcttcataca aaaacattta actagtgttt ttccagtttt gtgttcgttt cattttctca     720
ccaaactgac aataattact ttctgtgaac gtgttttgta ggcaagctcc cgaatatttt     780
tttctcttct cacgtcttgt tattttctcg attttatttt ctgaatctgt gcggttttca     840
atcaatttga ttgcgataat tattctatca gaaatatatt ttcagaaatc caaatactcc     900
aggtgccaat gcggtgaaag aaaattatga agtttattcc tgaaatcaca ctactcttgc     960
ttttatttgt acactctaca caggttagtt ggttgattct agatctcttg cctcctagct    1020
tgcaaggata atataattga attgttttg aggagtgcaa agattgaata gttttctata    1080
tttaggctaa aggaaaacga cggaaatgtc cggagggtgc gtggtcggaa ggaaagatta    1140
tgaacacgat catgagcaac tacacgaaaa tgttgcccga cgcggaggac agcgtacaag    1200
ttaatattga gattcatgta caggttggta gactctataa ttgcacacca atatgtgaaa    1260
gttttcttta aaattaaact gctgtaaatg acttttgaat aagtttatca gatagaaatt    1320
gtctgaactt tcgattcaa actttccgaa cttcaaagcg gttccaaatt actcacttcc    1380
atttatctct ttgctacaat ttctcccaca aagccttttt cttcatttaa cgttcttttt    1440
tatgtcgttg ttcttacaaa caatttcgtc tccttgatga actgcttgaa ctgagaatag    1500
```

-continued

```
tcacatgagg ataaattga tggaatgaca agttttgtgc ccagaaggca gttttgcact    1560
gaacttgttc agttgcagac acatctcaaa acacagaaga tgagtggaaa actagtgaga    1620
gactgccaaa agtcgaaggg ataatgaaaa tttgttgcaa atgaattctg cgaagttatg    1680
tgaaaaatta ttggattggg agttgtggga gtgaagagat gggtcaaaag ccatcaatct    1740
tgaatgcttc ggtcaaagat tgtttctca tatgtttaca acactgaaaa caatctatcc    1800
tagaaatgtt tgaaccaccc tctaaagtcc ttccgtatat tttttcatct ttataccgac    1860
cagaattcaa gagttgtttg aaataacttc ctcttttttg gagaatatgt actcagattt    1920
ttacattcaa aatttatata ttttcaaata gaaaagtgc caagtaccag aaactttat    1980 caagttggcg gcactttgga gagtgaattt gatgaaaaag tgtttgataa gtttgtcggg    2040
caaactggtc ccctgggtgg ggaaatggtg gcattttttgg aaacattttc atagtcgaag    2100
aagtggaaca agaaaattgg aaaatagaga tacatatgta tatgaaaata gaattgaaca    2160
ggaacttatt tttattttca ggatatggga agcttgaatg aaatatcatc cgactttgaa    2220
attgacattt tattcactca actgtggcat gactcggcac tttctttttgc tcatcttccg    2280 gcttgtaagc ggtaagaaat ctttgtatta gaagggaaaa atatttaaat taatgaaatt    2340
tcagaaatat cacaatggaa acacgacttt tacctaagat ttggtctcca aacacgtgta    2400
tgattaattc aaaacgaaca accgtccatg catcaccatc ggaaaatgtg atggttattc    2460
tgtacgaggt atgatttttg attttgtgac gtcacaaaca gagcatgtct aagggcatgt    2520
tgtagcaaga aaaaacgga ttcttgtctc tgtcgacgtt tcctaagtat tgtgaattat    2580
ttataataca tcactctaat tacgtgaata cttacacctt taactgggtg aaggataaaa    2640
tagagaagga gacgttgaaa aagctcttcg gtagattaaa gagtctagaa tcgacatatg    2700
tattcatgtt tctcggttca gggaaataag tgattttggc gaaaaagagt tagacgacat    2760 ttttttagaaa actaaaacta tattctcgaa cccaaatcag tctaatggtt ttcagcaaaa    2820
agtatgaaat atacaatgtt tgtttcagaa tacccagtac aaaaatttgaa gtttttcaga    2880 atggaacagt ctggattaac catcgtctta gtgtcaaatc accttgcaat ttggatctgc    2940
gacagtttcc tttcgatact caaacttgca tattaatctt tgaatcctat agtcataact    3000
cagaagaagt tgaacttcat tggatggaag aagctgtcac attaatgaag ccaattcaac    3060
ttcctgactt tgatatggtt cattattcaa ctaaaaagga aactttactc tatccaaacg    3120
ggtactggga tcagcttcaa gttactttca ctttcaaacg acgatatgga ttctatatta    3180
ttcaagccta tgttccaaca tatcttacaa tcattgtatc ttgggtttca ttctgcatgg    3240
aaccaaaagc tctgccggca agaacaactg tcggaatctc atctcttcta gctcttactt    3300
tccagtttgg aaatatttg aaaaatcttc caagggtttc atatgtgaaa ggtttgtttt    3360
ttttcttttt caaacaaata aaaaaaaga taaacaaata tttgtttcag caatggatgt    3420
gtggatgctt ggatgcatat catttgtctt cggaaccatg gtagaattgg catttgtttg    3480
ttacatttcc cgttgtcaga acagcgtaag aaagtgagtt ggcataagag ttttctcacg    3540
tggagggaag taattaaatt ttgggtgtca tatgaaaata tcaaaacaa tatcaggaaa    3600 ttgaatttca ctatgatttc gtagtaaaca aattacagcg cggaacgacg acgggaacga    3660
atgagaaatt ctcaggtgtg ggcaaacgga tcgtgtagaa ctagaagcaa cgggtatgca    3720
aacgggggat ctgtaatctc acattatcat ccaacaagca atggaaatgg gaataataat    3780
cgacatgata cacctcaagt tactggaagg ttagcaatct ctatgatagc atttatcaat    3840
tattaaagaa ctctggaatt agttttaaa gtataaataa atctctattt cttgcgacct    3900
```

-continued

```
acattgaact taatagttat gttttacaga ggatcacttc atcgaaacgg gccaccatct      3960
ccattaaacc ttcaaatgac tacatttgat tcggagatcc ctctgacttt tgatcaggtg      4020
agtcttacat tgagttcaaa cttttttgaat ttaagcgttc tatctgataa agttcttcgg     4080
tggttttata atttttgatt cataaactta cccactcctt tctcactaac attttaccct     4140
gttcagctgc cagtttccat ggaatccgat agaccctga ttgaagaggt aactgtgaaa       4200
gtagtcaatt aattccctgt gtttctaccc cactcaatcc ttttgtattt tttgttcagt     4260
ctatccacta tcaatgtctt atcacctcta gatactgttt agaagaaaat attgttcaca     4320
gttatggaaa tcacatatac tttgttctgg aattgtatat gtatgctttg aaaaagcaca     4380
ttagaatact acaaacatta gtttccatca gattttttgat ttatcaaaac cgttatatta    4440
gacactctta agttatcata ttctaatttc caagaatgtt atattttgaa gaagccggtg     4500
attgtcaaaa agattgaaaa ctccgagttt ctatatatgc gaaattttca cttcagccca     4560
cacacacaca cacacattca cgaaactttg tgttgtttat gttacttata tgttatcttt     4620
tctgtctgat catggttttc ggactgaaat tgtgttaatc ggaagttata tgtgagccac     4680
attgattaaa cctgtgagag atgcccattt gtactcattt tacgactgtc tcatgtccaa     4740
acaccatgtt tattgtaatt accaggctac tatttgcaga tgcgatcaac atcaccacct     4800
ccaccatctg gatgtctggc cagattccat ccggaagcag tggacaaatt ctccattgta     4860
gcttttccat tggcatttac aatgtttaat gttagttaat ccacagttaa aaattcccat     4920
aatcataaat atctcgactt ttcagcttgt ctactggtgg cactatttgt ctcaaacttt     4980
cgatcaaaac tatcagtgat tgaagtttat ccctttttaat tccataatt cacagttgcc      5040 ggtatctacc tccattcttt tccgatgatt cgcagttttt cacagggttc aaatgtatct     5100
cgttcaatct ttttatggtt atttctcttg aatgtccatt ttaatattta tagaacactt     5160
ttatgtacat tgtgttggta ttcaattcga aaaacaatga aatttatttc taaataactg     5220
cgtttctggg gtttctatca gcacttacta gctgacaaaa acttttccgt attcggaatt     5280
agatttttat gcaagcaatg tttcatttt acacagtata gtatttattc ttacttttga      5340
ttatattgct cgcaccctaa atgacaggta ttagaaatta accgcttttc agagtatttt     5400
taatcttctt agtactagtt tagttcttta aataagaaac catctagttt ttcattatca     5460
ctcaacttca gtcggacaaa ttttaaattt tttactcgat aaaaaaattt tataattcag     5520
acaaattatg tcttctcatt tttgatcgct                                      5550
```

<210> SEQ ID NO 2
<211> LENGTH: 1470
<212> TYPE: DNA
<213> ORGANISM: Caenorhabditis elegans

<400> SEQUENCE: 2

```
atgaagttta ttcctgaaat cacactactc ttgcttttat ttgtacactc tacacaggct       60
aaaggaaaac gacggaaatg tccggagggt gcgtggtcgg aaggaaagat tatgaacacg      120
atcatgagca actacacgaa aatgttgccc gacgcggagg acagcgtaca agttaatatt      180
gagattcatg tacaggatat gggaagcttg aatgaaatat catccgactt tgaaattgac      240
attttattca ctcaactgtg gcatgactcg gcactttctt ttgctcatct tccggcttgt      300
aagcgaaata tcacaatgga aacacgactt ttacctaaga tttggtctcc aaacacgtgt      360
atgattaatt caaaacgaac aaccgtccat gcatcaccat cggaaaatgt gatggttatt      420
```

-continued

```
ctgtacgaga atggaacagt ctggattaac catcgtctta gtgtcaaatc accttgcaat    480
ttggatctgc gacagtttcc tttcgatact caaacttgca tattaatctt tgaatcctat    540
agtcataact cagaagaagt tgaacttcat tggatggaag aagctgtcac attaatgaag    600
ccaattcaac ttcctgactt tgatatggtt cattattcaa ctaaaaagga aactttactc    660
tatccaaacg gtactgggga tcagcttcaa gttactttca cttcaaacg acgatatgga     720
ttctatatta ttcaagccta tgttccaaca tatcttacaa tcattgtatc ttgggtttca    780
ttctgcatgg aaccaaaagc tctgccggca agaacaactg tcggaatctc atctcttcta    840
gctcttactt tccagtttgg aaatattttg aaaaatcttc aagggtttc atatgtgaaa     900
gcaatggatg tgtggatgct tggatgcata tcatttgtct tcggaaccat ggtagaattg    960
gcatttgttt gttacatttc ccgttgtcag aacagcgtaa aaacgcgga acgacgacgg     1020
gaacgaatga gaaattctca ggtgtgggca acggatcgt gtagaactag aagcaacggg     1080
tatgcaaacg ggggatctgt aatctcacat tatcatccaa caagcaatgg aaatgggaat    1140
aataatcgac atgatacacc tcaagttact ggaagaggat cacttcatcg aaacgggcca    1200
ccatctccat taaaccttca aatgactaca tttgattcgg agatccctct gacttttgat    1260
cagctgccag tttccatgga atccgataga ccctgattg aagagatgcg atcaacatca     1320
ccacctccac catctggatg tctggccaga ttccatccgg aagcagtgga caaattctcc    1380
attgtagctt ttccattggc atttacaatg tttaatcttg tctactggtg gcactatttg    1440
tctcaaactt tcgatcaaaa ctatcagtga                                     1470
```

<210> SEQ ID NO 3
<211> LENGTH: 489
<212> TYPE: PRT
<213> ORGANISM: Caenorhabditis elegans

<400> SEQUENCE: 3

```
Met Lys Phe Ile Pro Glu Ile Thr Leu Leu Leu Leu Phe Val His
  1               5                  10                  15

Ser Thr Gln Ala Lys Gly Lys Arg Arg Lys Cys Pro Glu Gly Ala Trp
             20                  25                  30

Ser Glu Gly Lys Ile Met Asn Thr Ile Met Ser Asn Tyr Thr Lys Met
         35                  40                  45

Leu Pro Asp Ala Glu Asp Ser Val Gln Val Asn Ile Glu Ile His Val
     50                  55                  60

Gln Asp Met Gly Ser Leu Asn Glu Ile Ser Ser Asp Phe Glu Ile Asp
 65                  70                  75                  80

Ile Leu Phe Thr Gln Leu Trp His Asp Ser Ala Leu Ser Phe Ala His
                 85                  90                  95

Leu Pro Ala Cys Lys Arg Asn Ile Thr Met Glu Thr Arg Leu Leu Pro
            100                 105                 110

Lys Ile Trp Ser Pro Asn Thr Cys Met Ile Asn Ser Lys Arg Thr Thr
        115                 120                 125

Val His Ala Ser Pro Ser Glu Asn Val Met Val Ile Leu Tyr Glu Asn
    130                 135                 140

Gly Thr Val Trp Ile Asn His Arg Leu Ser Val Lys Ser Pro Cys Asn
145                 150                 155                 160

Leu Asp Leu Arg Gln Phe Pro Phe Asp Thr Gln Thr Cys Ile Leu Ile
                165                 170                 175

Phe Glu Ser Tyr Ser His Asn Ser Glu Glu Val Glu Leu His Trp Met
            180                 185                 190
```

```
Glu Glu Ala Val Thr Leu Met Lys Pro Ile Gln Leu Pro Asp Phe Asp
        195                 200                 205

Met Val His Tyr Ser Thr Lys Lys Glu Thr Leu Leu Tyr Pro Asn Gly
        210                 215                 220

Tyr Trp Asp Gln Leu Gln Val Thr Phe Thr Phe Lys Arg Arg Tyr Gly
225                 230                 235                 240

Phe Tyr Ile Ile Gln Ala Tyr Val Pro Thr Tyr Leu Thr Ile Ile Val
                245                 250                 255

Ser Trp Val Ser Phe Cys Met Glu Pro Lys Ala Leu Pro Ala Arg Thr
            260                 265                 270

Thr Val Gly Ile Ser Ser Leu Leu Ala Leu Thr Phe Gln Phe Gly Asn
        275                 280                 285

Ile Leu Lys Asn Leu Pro Arg Val Ser Tyr Val Lys Ala Met Asp Val
        290                 295                 300

Trp Met Leu Gly Cys Ile Ser Phe Val Phe Gly Thr Met Val Glu Leu
305                 310                 315                 320

Ala Phe Val Cys Tyr Ile Ser Arg Cys Gln Asn Ser Val Arg Asn Ala
                325                 330                 335

Glu Arg Arg Arg Glu Arg Met Arg Asn Ser Gln Val Trp Ala Asn Gly
            340                 345                 350

Ser Cys Arg Thr Arg Ser Asn Gly Tyr Ala Asn Gly Gly Ser Val Ile
        355                 360                 365

Ser His Tyr His Pro Thr Ser Asn Gly Asn Gly Asn Asn Asn Arg His
        370                 375                 380

Asp Thr Pro Gln Val Thr Gly Arg Gly Ser Leu His Arg Asn Gly Pro
385                 390                 395                 400

Pro Ser Pro Leu Asn Leu Gln Met Thr Thr Phe Asp Ser Glu Ile Pro
                405                 410                 415

Leu Thr Phe Asp Gln Leu Pro Val Ser Met Glu Ser Asp Arg Pro Leu
            420                 425                 430

Ile Glu Glu Met Arg Ser Thr Ser Pro Pro Pro Ser Gly Cys Leu
        435                 440                 445

Ala Arg Phe His Pro Glu Ala Val Asp Lys Phe Ser Ile Val Ala Phe
450                 455                 460

Pro Leu Ala Phe Thr Met Phe Asn Leu Val Tyr Trp Trp His Tyr Leu
465                 470                 475                 480

Ser Gln Thr Phe Asp Gln Asn Tyr Gln
                485

<210> SEQ ID NO 4
<211> LENGTH: 1417
<212> TYPE: DNA
<213> ORGANISM: Caenorhabditis elegans

<400> SEQUENCE: 4
tcatgtttca cggaacgacg aatttatccc gtcgtttctt cctttccgtt ttaactcata    60
tctcttcctg gatccttcag agctcttgtc aattcctcac gttttttttt gttttttcgt   120
cgtttaattg tggaaacaca tatccgtcct ctttgaaaca gcatcagaaa actttctgct   180
ctccgtgtcc ttctacttac tctgattgcc ttagttagtc acatcgcaag caacaactaa   240
ctgccaatgg gaggagccag ttggagcagg gtgcgtgctc ggtgctcttt tcagaaggtt   300
ttctcttgtg ccagcatgct ttttgaggc tgtgtcatca caatgaacat gtgtgagttc   360
atccgtctgg attattcttt tcttacgtc ttctgagtac ttcatacttt ccaaattttt   420
```

-continued

```
caactgaact tttcttcttt tctcattgaa gtggtttggt tttggtcgcg tgatcaacgg    480
atcctacttt tttgaaacaa aatgtttttg aagtttcaca gactgatttc ggggtttttt    540
caaagaatat attccctctc gagcaagaga aaattccaga aaatagtagt ttttttcaat    600
tagtcgtttc atttgtacta gctaaaaaac ttgcaactta tggctttaaa acatgtgttg    660
gcttcataca aaacattta actagtgttt ttccagtttt gtgttcgttt cattttctca    720
ccaaactgac aataattact ttctgtgaac gtgttttgta ggcaagctcc cgaatatttt    780
tttctcttct cacgtcttgt tatttttctcg attttatttt ctgaatctgt gcggttttca    840
atcaatttga ttgcgataat tattctatca gaaatatatt ttcagaaatc caaatactcc    900
aggtgccaat gcggtgaaag aaaattatga agtttattcc tgaaatcaca ctactcttgc    960
ttttatttgt acactctaca caggttagtt tctcttgaat gtccatttta atatttatag   1020 aacacttttta tgtacattgt gttggtattc aattcgaaaa acaatgaaat ttatttctaa   1080
ataactgcgt ttctggggtt tctatcagca cttactagct gacaaaaact tttccgtatt   1140
cggaattaga ttttttatgca agcaatgttt catttttaca cagtatagta tttattctta   1200
cttttgatta tattgctcgc accctaaatg acaggtatta gaaattaacc gcttttcaga   1260 gtattttttaa tcttcttagt actagtttag ttctttaaat aagaaaccat ctagttttc    1320 attatcactc aacttcagtc ggacaaattt taaatttttt actcgataaa aaatttttat   1380
aattcagaca aattatgtct tctcattttt gatcgct                            1417
```

<210> SEQ ID NO 5
<211> LENGTH: 5550
<212> TYPE: DNA
<213> ORGANISM: Caenorhabditis elegans

<400> SEQUENCE: 5

```
tcatgtttca cggaacgacg aatttatccc gtcgtttctt cctttccgtt ttaactcata      60
tctcttcctg gatccttcag agctcttgtc aattcctcac gttttttttt gtttttttcgt    120 cgtttaattg tggaaacaca tatccgtcct ctttgaaaca gcatcagaaa actttctgct    180
ctccgtgtcc ttctacttac tctgattgcc ttagttagtc acatcgcaag caacaactaa    240
ctgccaatgg gaggagccag ttggagcagg tgcgtgctc ggtgctcttt tcagaaggtt     300
ttctcttgtg ccagcatgct ttttgaggc tgtgtcatca caatgaacat gtgtgagttc     360
atccgtctgg attattcttt ttcttacgtc ttctgagtac ttcatacttt ccaaattttt    420
caactgaact tttcttcttt tctcattgaa gtggtttggt tttggtcgcg tgatcaacgg    480
atcctacttt tttgaaacaa aatgtttttg aagtttcaca gactgatttc ggggtttttt    540
caaagaatat attccctctc gagcaagaga aaattccaga aaatagtagt ttttttcaat    600
tagtcgtttc atttgtacta gctaaaaaac ttgcaactta tggctttaaa acatgtgttg    660
gcttcataca aaacattta actagtgttt ttccagtttt gtgttcgttt cattttctca    720
ccaaactgac aataattact ttctgtgaac gtgttttgta ggcaagctcc cgaatatttt    780
tttctcttct cacgtcttgt tatttttctcg attttatttt ctgaatctgt gcggttttca    840
atcaatttga ttgcgataat tattctatca gaaatatatt ttcagaaatc caaatactcc    900
aggtgccaat gcggtgaaag aaaattatga agtttattcc tgaaatcaca ctactcttgc    960
ttttatttgt acactctaca caggttagtt ggttgattct agatctcttg cctcctagct   1020
tgcaaggata atataattga attgttttttg aggagtgcaa agattgaata gttttctata  1080
```

```
tttaggctaa aggaaaacga cggaaatgtc cggagggtgc gtggtcggaa ggaaagatta   1140
tgaacacgat catgagcaac tacacgaaaa tgttgcccga cgcggaggac agcgtacaag   1200
ttaatattga gattcatgta caggttggta gactctataa ttgcacacca atatgtgaaa   1260 gttttctttta aaattaaact gctgtaaatg acttttgaat aagtttatca gatagaaatt   1320
gtctgaactt ttcgattcaa actttccgaa cttcaaagcg gttccaaatt actcacttcc   1380
atttatctct ttgctacaat ttctcccaca aagccttttt cttcatttaa cgttcttttt   1440
tatgtcgttg ttcttacaaa caatttcgtc tccttgatga actgcttgaa ctgagaatag   1500
tcacatgagg ataaatttga tggaatgaca gttttgtgc ccagaaggca gttttgcact   1560
gaacttgttc agttgcagac acatctcaaa acacagaaga tgagtggaaa actagtgaga   1620
gactgccaaa agtcgaaggg ataatgaaaa tttgttgcaa atgaattctg cgaagttatg   1680
tgaaaaatta ttggattggg agttgtggga gtgaagagat gggtcaaaag ccatcaatct   1740
tgaatgcttc ggtcaaagat ttgtttctca tatgtttaca acactgaaaa caatctatcc   1800
tagaaatgtt tgaaccaccc tctaaagtcc ttccgtatat ttttcatct ttataccgac    1860 cagaattcaa gagttgtttg aaataacttc ctctttttg gagaatatgt actcagattt    1920
ttacattcaa aatttatata ttttcaaata gaaaagtgc caagtaccag aaactttat    1980 caagttggcg gcactttgga gagtgaattt gatgaaaag tgtttgataa gtttgtcggg   2040
caaactggtc ccctgggtgg ggaaatggtg gcatttttgg aaacattttc atagtcgaag   2100
aagtggaaca agaaaattgg aaaatagaga tacatatgta tatgaaaata gaattgaaca   2160
ggaacttatt tttattttca ggatatggga agcttgaatg aaatatcatc cgactttgaa   2220
attgacattt tattcactca actgtggcat gactcggcac tttctttttgc tcatcttccg   2280 gcttgtaagc ggtaagaaat ctttgtatta gaagggaaaa atatttaaat taatgaaatt   2340
tcagaaatat cacaatggaa acacgacttt tacctaagat ttggtctcca aacacgtgta   2400
tgattaattc aaaacgaaca accgtccatg catcaccatc ggaaaatgtg atggttattc   2460
tgtacgaggt atgatttttg attttgtgac gtcacaaaca gagcatgtct aagggcatgt   2520
tgtagcaaga aaaaacgga ttcttgtctc tgtcgacgtt tcctaagtat tgtgaattat    2580
ttataataca tcactctaat tacgtgaata cttacacctt taactgggtg aaggataaaa   2640
tagagaagga gacgttgaaa aagctcttcg gtagattaaa gagtctagaa tcgacatatg   2700
tattcatgtt tctcggttca gggaaataag tgattttggc gaaaaagagt tagacgacat   2760
tttttagaaa actaaaacta tattctcgaa cccaaatcag tctaatggtt ttcagcaaaa   2820
agtatgaaat atacaatgtt tgtttcagaa tacccagtac aaaatttgaa gtttttcaga   2880
atggaacagt ctggattaac catcgtctta gtgtcaaatc accttgcaat ttggatctgc   2940 gacagttttcc tttcgatact caaacttgca tattaatctt tgaatcctat agtcataact   3000
cagaagaagt tgaacttcat tggatggaag aagctgtcac attaatgaag ccaattcaac   3060
ttcctgactt tgatatggtt cattattcaa ctaaaaagga aactttactc tatccaaacg   3120
ggtactggga tcagcttcaa gttactttca ctttcaaacg acgatatgga ttctatatta   3180
ttcaagccta tgttccaaca tatcttacaa tcattgtatc ttgggtttca ttctgcatgg   3240
aaccaaaagc tctgccggca agaacaactg tcggaatctc atctcttcta gttcttactt   3300
tccagtttgg aaatattttg aaaaatcttc caagggtttc atatgtgaaa ggtttgtttt   3360 ttttctttttt caaacaaata aaaaaaaaga taaacaaata tttgtttcag caatggatgt   3420
gtggatgctt ggatgcatat catttgtctt cggaaccatg gtagaattgg catttgtttg   3480
```

-continued

| | |
|---|---|
| ttacatttcc cgttgtcaga acagcgtaag aaagtgagtt ggcataagag ttttctcacg | 3540 |
| tggagggaag taattaaatt ttgggtgtca tatgaaaata tcaaaaacaa tatcaggaaa | 3600 |
| ttgaatttca ctatgatttc gtagtaaaca aattacagcg cggaacgacg acggaacga | 3660 |
| atgagaaatt ctcaggtgtg ggcaaacgga tcgtgtagaa ctagaagcaa cgggtatgca | 3720 |
| aacgggggat ctgtaatctc acattatcat ccaacaagca atggaaatgg gaataataat | 3780 |
| cgacatgata cacctcaagt tactggaagg ttagcaatct ctatgatagc atttatcaat | 3840 |
| tattaaagaa ctctggaatt agttttaaa gtataaataa atctctatt cttgcgacct | 3900 |
| acattgaact taatagttat gttttacaga ggatcacttc atcgaaacgg ccaccatct | 3960 |
| ccattaaacc ttcaaatgac tacatttgat tcggagatcc ctctgacttt tgatcaggtg | 4020 |
| agtcttacat tgagttcaaa cttttgaat ttaagcgttc tatctgataa agttcttcgg | 4080 |
| tggtttata attttgatt cataaactta cccactcctt tctcactaac attttaccct | 4140 |
| gttcagctgc cagtttccat ggaatccgat agacccctga ttgaagaggt aactgtgaaa | 4200 |
| gtagtcaatt aattccctgt gtttctaccc cactcaatcc ttttgtattt tttgttcagt | 4260 |
| ctatccacta tcaatgtctt atcacctcta gatactgttt agaagaaaat attgttcaca | 4320 |
| gttatggaaa tcacatatac tttgttctgg aattgtatat gtatgctttg aaaagcaca | 4380 |
| ttagaatact acaaacatta gttccatca gattttgat ttatcaaaac cgttatatta | 4440 |
| gacactctta agttatcata ttctaattc caagaatgtt atattttgaa gaagccggtg | 4500 |
| attgtcaaa agattgaaaa ctccgagttt ctatatatgc gaaattttca cttcagccca | 4560 |
| cacacacaca cacacattca cgaaactttg tgttgtttat gttacttata tgttatcttt | 4620 |
| tctgtctgat catggttttc ggactgaaat tgtgttaatc ggaagttata tgtgagccac | 4680 |
| attgattaaa cctgtgagag atgcccattt gtactcattt tacgactgtc tcatgtccaa | 4740 |
| acaccatgtt tattgtaatt accaggctac tatttgcaga tgcgatcaac atcaccacct | 4800 |
| ccaccatctg gatgtctggc cagattccat ccggaagcag tggacaaatt ctccattgta | 4860 |
| gcttttccat tggcatttac aatgtttaat gttagttaat ccacagttaa aaattcccat | 4920 |
| aatcataaat atctcgactt ttcagcttgt ctactggtgg cactatttgt ctcaaacttt | 4980 |
| cgatcaaaac tatcagtgat tgaagtttat ccctttaat tccaataatt cacagttgcc | 5040 |
| ggtatctacc tccattcttt tccgatgatt cgcagttttt cacagggttc aaatgtatct | 5100 |
| cgttcaatct ttttatggtt atttctcttg aatgtccatt ttaatattta tagaacactt | 5160 |
| ttatgtacat tgtgttggta ttcaattcga aaacaatga aatttatttc taaataactg | 5220 |
| cgtttctggg gtttctatca gcacttacta gctgacaaaa acttttccgt attcggaatt | 5280 |
| agatttttat gcaagcaatg tttcattttt acacagtata gtatttattc ttacttttga | 5340 |
| ttatattgct cgcaccctaa atgacaggta ttagaaatta accgcttttc agagtatttt | 5400 |
| taatcttctt agtactagtt tagttcttta aataagaaac catctagttt ttcattatca | 5460 |
| ctcaacttca gtcggacaaa ttttaaattt tttactcgat aaaaaaattt tataattcag | 5520 |
| acaaattatg tcttctcatt tttgatcgct | 5550 |

<210> SEQ ID NO 6
<211> LENGTH: 1470
<212> TYPE: DNA
<213> ORGANISM: Caenorhabditis elegans

<400> SEQUENCE: 6

-continued

```
atgaagttta ttcctgaaat cacactactc ttgcttttat ttgtacactc tacacaggct    60
aaaggaaaac gacggaaatg tccggagggt gcgtggtcgg aaggaaagat tatgaacacg   120
atcatgagca actacacgaa aatgttgccc gacgcggagg acagcgtaca agttaatatt   180
gagattcatg tacaggatat gggaagcttg aatgaaatat catccgactt tgaaattgac   240
attttattca ctcaactgtg gcatgactcg gcactttctt ttgctcatct tccggcttgt   300
aagcgaaata tcacaatgga aacacgactt ttacctaaga tttggtctcc aaacacgtgt   360
atgattaatt caaaacgaac aaccgtccat gcatcaccat cggaaaatgt gatggttatt   420
ctgtacgaga atggaacagt ctggattaac catcgtctta gtgtcaaatc accttgcaat   480
ttggatctgc gacagtttcc tttcgatact caaacttgca tattaatctt tgaatcctat   540
agtcataact cagaagaagt tgaacttcat tggatggaag aagctgtcac attaatgaag   600
ccaattcaac ttcctgactt tgatatggtt cattattcaa ctaaaaagga aactttactc   660
tatccaaacg ggtactggga tcagcttcaa gttactttca ctttcaaacg acgatatgga   720
ttctatatta ttcaagccta tgttccaaca tatcttacaa tcattgtatc ttgggtttca   780
ttctgcatgg aaccaaaagc tctgccggca agaacaactg tcggaatctc atctcttcta   840
gttcttactt tccagtttgg aaatatttg aaaaatcttc aagggtttc atatgtgaaa    900
gcaatggatg tgtggatgct tggatgcata tcatttgtct tcggaaccat ggtagaattg   960
gcatttgttt gttacatttc ccgttgtcag aacagcgtaa gaaacgcgga acgacgacgg  1020
gaacgaatga gaaattctca ggtgtgggca aacggatcgt gtagaactag aagcaacggg  1080
tatgcaaacg ggggatctgt aatctcacat tatcatccaa caagcaatgg aaatgggaat  1140
aataatcgac atgatacacc tcaagttact ggaagaggat cacttcatcg aaacgggcca  1200
ccatctccat taaaccttca aatgactaca tttgattcgg agatccctct gacttttgat  1260
cagctgccag tttccatgga atccgataga cccctgattg aagagatgcg atcaacatca  1320
ccacctccac catctggatg tctggccaga ttccatccgg aagcagtgga caaattctcc  1380
attgtagctt ttccattggc atttacaatg tttaatcttg tctactggtg gcactatttg  1440
tctcaaactt tcgatcaaaa ctatcagtga                                   1470
```

US 7,026,466 B1

SEROTONIN-GATED ANION CHANNEL

CROSS REFERENCE TO RELATED APPLICATIONS

This application is a continuation-in-part application of U.S. Ser. No. 09/559,622, filed Apr. 27, 2000 now U.S. Pat. No. 6,812,376, which claims priority from U.S. Provisional Application Ser. No. 60/131,149, filed Apr. 27, 1999.

STATEMENT AS TO FEDERALLY SPONSORED RESEARCH

This research has been funded by NIH Grant R37GM24663. The U.S. government has certain rights to the invention.

BACKGROUND OF THE INVENTION

The invention relates to the diagnosis and treatment of conditions associated with serotonin-mediated cellular responses.

The biogenic amine serotonin plays a role in the modulation of neuronal synaptic events as well as non-neuronal cellular signaling. Serotonin acts by binding to receptors on a variety of cells. These receptors fall into two broad functional and structural categories, those acting through G-proteins to mediate intracellular signaling, and those that form ion channels. It is generally believed that serotonin may act by binding to either G-protein-coupled seven-pass transmembrane receptors, or serotonin-gated cation channels. There are six major classes of G-protein-coupled receptors, each with numerous subtypes. Thus far, there is only one class of serotonin-gated ion channels, the 5-$HT_3$ receptor. G-protein-coupled responses can be either excitatory or inhibitory upon activation by serotonin. Activation of G-protein-coupled receptors by serotonin generally mediates responses which are slower-acting and longer-lasting, while ion channels mediate fast-acting and transitory responses. The 5-$HT_3$ receptor, comprised of the conducting subunit, 5-$HT_{3a}$ and a regulatory subunit, 5-$HT_{3b}$, appears to exclusively elicit excitatory responses that are generally fast-acting and transitory.

The 5-$HT_3$ receptor is selectively permeable to cations only, such as $Na^+$ or $K^+$, and is very slightly permeable to $Ca^{2+}$. The influx of cations, such as $Na^+$ into a cell results in depolarization and excitatory neurotransmission. Efflux of cations, such as $K^+$ hyperpolarizes the cell, thereby reducing the likelihood of excitation, and generally leads to inhibitory neurotransmission. Since the resting membrane of a typical cell/neuron is much less permeable to $Na^+$ influx than to $K^+$ efflux, the opening of a non-selective $Na^+/K^+$ channel, such as the 5-$HT_3$ receptor leads to a dramatic influx of $Na^+$, leading to depolarization and excitation.

Serotonin has been implicated in the etiology of many disease states, including depression, panic disorders, obsessive compulsive disorder, cardiac abnormalities, sleep disorders, eating disorders, nausea and vomiting, gastrointestinal cramps, and migraines. G-protein-coupled serotonin receptors have been implicated in the control of mood (5-$HT_{1A}$), migraine (5-$HT_{1B}$), pain perception (5-$HT_{1D}$), smooth muscle contraction (5-$HT_{2A}$, 5-$HT_7$), anxiety (5-$HT_{2C}$), and nausea (5-$HT_4$). Activation of the 5-$HT_3$ receptor by serotonin can either stimulate or inhibit cardiac function, induce vasodilation, affect lung and intestinal function, cause pain and sensitization of nociceptive neurons, and induce nausea and vomiting. Not surprisingly, many treatments for these disorders are thought to act through serotonergic pathways.

Several classes of drugs thought to modulate the serotonergic pathway exist. For example, selective serotonin re-uptake inhibitors (SSRIs) are used to treat depression. These antidepressants, including Prozac, Zoloft, and Paxil, are believed to act by potentiating serotonin levels at the synapse. Drugs, such as Imitrex, used to treat migraine headaches, act as selective serotonin receptor agonists. Other groups of drugs used to affect mood include monoamine oxidase inhibitors, and selective serotonin receptor antagonists.

While these drugs are administered to humans to treat the above-described disease states, the patients often unpredictably experience a number of side-effects including insomnia, anxiety, chest pain, hypertension, nausea, anorexia, sweating, chills, vomiting, diarrhea, constipation, decreased libido, and abnormal ejaculation. It has been hypothesized that the side-effects result from multiple receptor activation or inactivation when a serotonin agonist or antagonist is given as a treatment. Some of these improperly activated or inactivated receptors may lead to fast- or slow-acting excitatory responses, or slow-acting inhibitory responses, when really only one specific type of response is desired.

A better understanding of serotonin-associated cellular communication could greatly facilitate the discovery of drugs and therapeutic methodologies to treat a broad range of conditions with fewer of the serious and variable side-effects prevalent with currently available drugs that interface with the serotonin pathway. Exactly how the currently available drugs that interface with the serotonin pathway work is not well understood. Agonists, antagonists, and especially serotonin re-uptake inhibitors could affect numerous serotonin receptor subtypes, and the final outcome may be a combined readout of all these varied, and sometimes antagonistic, pathways. It has been hypothesized that the various undesirable side-effects of a given drug's action are the result of unwanted activation of the serotonin pathways that are not specific to the condition being treated. Therefore, compounds with a greater specificity for a specific serotonin receptor, for a limited subset of serotonin receptors, or for a specific subtype of a particular class of serotonin receptors would be invaluable to the field of therapeutics for serotonin-mediated disease states.

SUMMARY OF THE INVENTION

We have discovered a serotonin-gated ion channel, MOD-1, that is exclusively permeable to chloride ions, and is not permeable to sodium, potassium, or calcium ions. Activation of this anion channel is most likely to result in an inhibitory response. In some circumstances that are dependent on the reversal potential for chloride (which is a function of the concentration of chloride inside and outside the cell) activation of anion channels could result in an excitatory response. Therefore, it is conceivable that activation of a serotonin-gated anion channel could also result in excitatory neurotransmission.

With the discovery of MOD-1 and the serotonin-gated anion channel that it forms, comes the realization that serotonin may mediate fast-acting, and transitory, inhibitory responses in addition to excitatory responses. It is possible that the activation/inactivation of a MOD-1-like serotonin-gated anion channel, in humans, is associated with some of the effects and/or side-effects of existing serotonin-based drugs. It is also conceivable that many of the serotonin-related diseases are exclusively due to defects in, or associated with, a serotonin-gated anion channel. None of the currently available drugs have been designed to effectively and specifically target this receptor. Therefore, the discoveries of a serotonin-gated anion channel and the gene that encodes it are invaluable tools for use in discovering diagnostic and therapeutic compounds for the detection and treatment of conditions associated with serotonin-mediated cellular responses.

One way in which a serotonin-gated anion channel can be used as a tool in drug discovery is by screening existing drugs or drug candidates for their effects on serotonin-gated anion channel activity. Such an experiment can be done using MOD-1 or other serotonin-gated anion channels from non-mammals, such as nematodes, or from lower mammals or humans. Understanding how drugs affect, or do not affect, this anion channel will lend better insight into the overall effect of a drug's mechanism of action. Also, a better understanding of how this serotonin-gated anion channel is regulated will contribute to a better understanding of how current therapies work. Furthermore, information gained from this screen will permit the development of drugs with higher specificities for a particular type of serotonin-binding receptor that will mediate only the desired response. Such drugs include those which do not activate a serotonin-gated anion channel, but do activate other serotonin receptors; those that act specifically on a serotonin-gated anion channel, but not on other serotonin receptors; or those that activate a subset of the various serotonin receptors.

Methods of drug discovery are not limited to screening available drugs only, but also to all compounds and their derivatives that were extracted or synthesized during the development of a given drug affecting serotonin-mediated cellular processes. Furthermore, a de novo screen of chemicals can be conducted, with no bias regarding possible functional relevance, for effects on this class of serotonin-gated anion channels.

In a first aspect, the invention features a substantially pure polypeptide that is a serotonin-gated anion channel. In one embodiment, the polypeptide is a substantially pure serotonin-gated anion channel that is permeable to chloride ions. In another embodiment, the polypeptide is MOD-1. In a further embodiment, the polypeptide is a subunit that makes up a multi-subunit serotonin-gated anion channel, permeable to chloride ions. Preferably this polypeptide is from *Caenorhabditis elegans* (*C. elegans*). More preferably this polypeptide is mammalian. Most preferably this polypeptide is human.

In still another embodiment of the invention, the serotonin-gated anion channel is activated by a lower concentration of serotonin than that required to activate the 5-HT$_3$ receptor. For example, the serotonin-gated anion channel may have a higher binding affinity for serotonin than the 5-HT$_3$ receptor. This higher affinity can be assessed by calculating and comparing the dissociation constants of serotonin binding to the 5-HT$_3$ receptor and to a serotonin-gated anion channel.

In another aspect, the invention features a substantially pure nucleic acid sequence encoding a serotonin-gated anion channel. In one embodiment, the substantially pure nucleic acid sequence encodes a serotonin-gated anion channel that is permeable to chloride ions. In another embodiment, the nucleic acid sequence is mod-1, and encodes the MOD-1 polypeptide. Preferably this nucleic acid sequence is from *C. elegans*. More preferably the nucleic acid sequence is mammalian. Most preferably the nucleic acid sequence is human.

In another aspect, the invention features an antibody that preferably specifically binds to a serotonin-gated anion channel. In one embodiment, the antibody binds to a serotonin-gated anion channel that is permeable to chloride ions. This invention includes polyclonal, as well as monoclonal antibodies to the serotonin-gated anion channel.

In another aspect, the invention features a *C. elegans* strain having a mutant mod-1 gene. In one embodiment of the invention, the *C. elegans* strain has a mutant mod-1 gene that does not function as a chloride channel. In another embodiment, the strain has a mutant mod-1 gene that acts in a dominant-negative manner. In another embodiment, the strain has a mutant mod-1 gene that encodes a polypeptide that is constitutively active.

In another aspect, the invention features a method for identifying a compound that modulates the biological activity of a serotonin-gated anion channel. The method includes the steps of: (a) administering a test compound to a serotonin-gated anion channel, and (b) assaying a modulation in the biological activity of a serotonin-gated anion channel. Assaying the modulation of biological activity may be done by measuring the current carried through a channel, or by measuring the amount of serotonin binding to a serotonin-gated anion channel. The assay can also be a bioassay that involves measuring the rate of locomotion in nematodes having a serotonin-gated anion channel. In one embodiment, the serotonin-gated anion channel is from nematodes. In another embodiment, the serotonin-gated anion channel is from a rat, mouse, or human, and is inserted into a *C. elegans* that either has or does not have a wild-type *C. elegans* serotonin-gated anion channel. In another embodiment, the serotonin-gated anion channel is a chimeric molecule between the serotonin-gated anion channels from various species. In further various embodiments of this aspect, the channel is in a cell, for example, a neuron or a non-neuronal cell. The channel may also be in a lipid bi-layer, a mammal, or a nematode. In yet another embodiment, the serotonin-gated anion channel comprises sufficient MOD-1 protein to form a serotonin-gated anion channel.

In the above aspect of the invention, the test compound is administered in the absence or presence of serotonin, and is administered prior to, simultaneously with, or after administration of serotonin. Administration may also be in the absence or presence of known drugs that interface with the serotonin pathway. The modulation of the biological activity may be either agonistic or antagonistic. The compound may also be a cell lysate, or isolated from a cell lysate, and may be administered prior to, simultaneously with, or after administration of serotonin, or any known effector of serotonin-mediated cellular processes.

In another aspect, the invention features a method for treating a condition in a patient by administering an agonist or antagonist of a serotonin-gated anion channel to the patient. Conditions that are treated include migraine headaches, loss of appetite, gain of appetite, insomnia, inability to wake up, memory loss, inability to learn, nausea and vomiting, gastrointestinal cramps, body temperature deregulation, moods, including depression or mania, abnormal sexual or hallucinogenic behavior, abnormal cardiovascular function, abnormal muscle contraction, and abnormal endocrine regulation.

In another aspect, the invention features a diagnostic probe for measurement of a serotonin-gated anion channel, either wild-type or mutant, for detecting conditions associated with serotonin-mediated cellular responses. Measurement of a serotonin-gated anion channel includes, but is not limited to detection of nucleic acid levels that code for a serotonin-gated anion channel, levels of a polypeptide that can function as a serotonin-gated anion channel, single strand confirmation polymorphism analyses, or the flow of current across a membrane. In one embodiment, the probe is a nucleic acid sequence that encodes a serotonin-gated anion channel, for example, MOD-1, or a polypeptide that is a serotonin-gated anion channel, or an antibody that binds to a serotonin-gated anion channel. In yet another embodiment, the probe is standard electrophysiology voltage clamping equipment that measure the activity of a serotonin-gated anion channel. In still another embodiment, the diagnostic probe is used for pharmacogenetics, i.e., in the analyses of conditions associated with serotonin-mediated cellular responses within an individual, family, or families.

In another aspect, the invention features a method for characterizing drugs associated with serotonin-mediated cellular responses, by measuring serotonin-gated anion channel activity upon drug exposure. The drugs include those already currently available for the treatment of serotonin-mediated responses, as well as small molecules that are similar in structure to these drugs. This invention also includes the discovery of any compounds which have not yet been identified as therapeutic for serotonin-mediated cellular responses.

In another aspect, the invention features a method for decreasing serotonin-gated anion channel function by decreasing the level of a serotonin-gated anion channel polypeptide with antisense RNA to the serotonin-gated anion channel, and the antisense RNA itself. Preferably the level of the serotonin-gated anion channel is deceased at least 25%, more preferably at least 50%, 70%, or 80%, and most preferably at least 95%, compared to a control (e.g., a serotonin-gated anion channel that is not contacted with an antisense RNA, or that is contacted with a nonsense RNA sequence). In addition, preferably the antisense RNA is antisense mod-1 RNA. Such nucleic acids of the invention and methods for using them may be identified according to a method involving: (a) providing a cell sample; (b) introducing by transformation into the cell sample, a test nucleic acid sequence for a serotonin-gated anion channel; (c) expressing the test nucleic acid of a serotonin-gated anion channel within the cell sample; and (d) determining whether the cell sample exhibits altered serotonin-gated anion channel activity, whereby either increased or decreased channel activity identifies a nucleic acid which may be used to alter serotonin-gated anion channel function. Preferably the cell is a non-neuronal cell. Most preferably the cell is a neuronal cell.

In another aspect, the invention features a method for decreasing the function of a serotonin-gated anion channel by administering an antibody that specifically binds to a serotonin-gated anion channel, or binds to a peptide from that channel. This method includes, but is not limited to, using an antibody to MOD-1 as the antibody, and a channel formed by any MOD-1 polypeptide as the channel whose function is inhibited. The methods also includes using a mammalian antibody to decrease the function of a mammalian serotonin-gated anion channel. This method also includes administration of the antibody in vivo or in vitro.

In another aspect, the invention features a method for modulating serotonin-gated anion channel activity using a nucleic acid vector encoding a serotonin-gated anion channel, and administering enough vector to alter activity of the serotonin-gated anion channels of at least one cell. In one embodiment, the vector is operably linked to a promoter. In other embodiments, the vector encodes a wild-type serotonin-gated anion channel or a mutant serotonin-gated anion channel. The mutant serotonin-gated anion channel may include, but is not limited to, a mutant channel that is a loss-of-function mutant, a dominant negative mutant, or a constitutively active mutant. In a preferred embodiment, the nucleic acid vector encodes a wild-type or mutant MOD-1 polypeptide. In other embodiments, administration may occur in vitro or in vivo. In further embodiments, the vector encodes a polypeptide that affects the function of a serotonin-gated anion channel, or that affects molecules that are targeted subsequent to activation of a serotonin-gated anion channel. These molecules include, but are not limited to, protein kinases, protein phosphatases, and proteases.

In another aspect, the invention features a method for testing a patient having a serotonin-mediated condition, for his/her pre-disposition to respond to therapy, or to experience side-effects due to administration of a specific therapy.

The method comprises:
(a) determining the characteristics of a serotonin-gated anion channel from tissues of the patient, where the characteristics are indicative of the abnormal activity of a serotonin-gated anion channel; and
(b) administering to the patient a suitable therapeutic agent relative to the degree of abnormal activity of the serotonin-gated anion channel in step (a).

In various embodiments, the abnormal activity is due to mutations in a serotonin-gated anion channel protein, altered levels of synthesis of mRNA of a serotonin-gated anion channel, altered serotonin-gated anion channel protein levels in tissues. In another embodiment, the method further comprises characterizing other serotonin-mediated receptors in the patients. Therapeutic agents to be used in accordance with the present invention may be selected from the group consisting of inhibitors or activators of serotonin-mediated pathways, including therapeutics which are currently available, as well as those which are discovered, as described herein.

In accordance with the present invention, there is provided a method for the identification of a patient possessing a serotonin-mediated condition to be responsive to therapies for the condition, or to experience side-effects due to administration of a specific therapy. This method comprises:
(a) determining the characteristics of a serotonin-gated anion channel gene allele in a biological sample of the patient directly, using appropriate probes to a serotonin-gated anion channel, or indirectly, by phenotyping, and;
(b) correlating the genotype or phenotype with appropriated drug and/or dosage.

The presence or absence of a specific serotonin-gated anion channel allele indicates a predisposition, or lack thereof, to respond to serotonin-mediated therapies.

In another aspect, the invention claims a method for identifying a gene that is structurally related to a serotonin-gated anion channel. This method involves identifying a gene by designing probes or primers, including degenerate oligonucleotides, to specific sequences. These primers or probes encode structurally significant amino acid sequence (e.g., the sequence that forms the transmembrane portions of the serotonin-gated anion channel), and are used to screen large genomic or cDNA libraries. If a PCR approach is utilized, the primers are optionally designed to allow cloning of the amplified product into a suitable vector. PCR is particularly useful for screening cDNA libraries from rare tissue types. The method also includes identifying a gene using antibodies, using nucleic acid or amino acid scanning databases and computer programs, and screening for genes that function in a manner similar to, or different from, a serotonin-gated anion channel.

In a related aspect, the invention features the nucleic acid sequence identified by the method of identifying a gene which is structurally related to a serotonin-gated anion channel. This gene may be isolated from nematodes or mammals, preferably from rodents, and most preferably from human.

In another aspect, the invention features a transgenic, or other mutant animal, that over-expresses or under-expresses a serotonin-gated anion channel, or expresses a dominant-negative serotonin-gated anion channel. The invention includes a nematode or a non-human mammal, for example, a mouse, as the animal. In one embodiment, the animal over-expresses a serotonin-gated anion channel that is constitutively active.

In two additional aspects, the invention features a transgenic animal and methods of using the animal for the detection of therapeutics for conditions associated with serotonin-mediated cellular responses. Preferably the animal over-expresses a serotonin-mediated anion channel polypeptide, either wild-type or mutant, or expresses an antisense RNA to a serotonin-gated anion channel or a serotonin-gated anion channel fragment. In one embodiment, the animal also has a genetic predisposition to conditions associated with serotonin-mediated cellular responses.

In yet another aspect, the invention features a method for identifying a compound that modulates the activity of a serotonin-gated anion channel by exposing a nematode to a test compound, assaying the rate of locomotion, and comparing the locomotion rate to that of a nematode receiving no test compound, serotonin, or a placebo, where a modulation in the rate of locomotion indicates a compound that modulates the activity of a serotonin-gated anion channel. The test compound may be applied at various concentrations. In addition, the nematodes used in the screen may be bacterial-lawn deprived prior to beginning the screen.

In still another aspect, the invention features a method for identifying a compound that modulates the activity of a serotonin-gated anion channel. The method involves exposing a nematode to a test compound, quantifying the number of nematodes actively swimming after exposure to the compound, and comparing that number to that of a control receiving no test compound, serotonin, or a placebo, where a modulation in the number of actively swimming nematodes indicates a compound that modulates the activity of a serotonin-gated anion channel. The test compound may be applied at various concentrations. In addition, the nematodes used in the screen may be bacterial-lawn deprived prior to beginning the screen.

By "treatment" is meant the submission or subjection of an animal, cell, lysate or extract derived from a cell, or molecule derived from a cell to a test compound or stimulus to a serotonin-mediated response.

By a "test compound" is meant a chemical, be it naturally-occurring or artificially-derived, that is surveyed for its ability to modulate serotonin-mediated cellular responses, by employing one of the assay methods described herein. Test compounds may include, for example, peptides, polypeptides, synthetic organic molecules, naturally occurring organic molecules, nucleic acid molecules, and components thereof.

By "treat" is meant to submit or subject an animal, cell, lysate or extract derived from a cell, or molecule derived from a cell to a test compound or stimulus to a serotonin-mediated response.

By a "substantially pure polypeptide" is meant a polypeptide that has been separated from the components that naturally accompany it. Typically, the polypeptide is substantially pure when it is at least 60%, by weight, free from the proteins and naturally-occurring organic molecules with which it is naturally associated. Preferably the polypeptide is a serotonin-gated anion channel polypeptide that is at least 75%, more preferably at least 90%, and most preferably at least 99%, by weight, pure. A substantially pure serotonin-gated anion channel polypeptide may be obtained, for example, by extraction from a natural source (e.g., a neuronal or smooth muscle cell), by expression of a recombinant nucleic acid encoding a serotonin-gated anion channel polypeptide, or by chemically synthesizing the protein. Purity can be assayed by any appropriate method, e.g., by column chromatography, polyacrylamide gel electrophoresis, agarose gel electrophoresis, optical density, or HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes.

By a "purified nucleic acid" is meant a nucleic acid that is free of the genes which, in the naturally-occurring genome of the organism from which the nucleic acid of the invention is derived, flank the gene. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic or cDNA fragment produced by PCR or restriction endonuclease digestion) independent of other sequences. It also includes recombinant DNA that is part of a hybrid gene encoding additional polypeptide sequence.

By a "serotonin-gated anion channel" is meant a channel whose opening is regulated by serotonin binding to the channel. The opening of the channel selectively permits passage of anions from one side of the channel to the other. In one embodiment, the anion is chloride. Preferably the nucleic acid sequence encoding a serotonin-gated anion channel hybridizes to a mod-1 nucleic acid sequence.

By a "mod-1 gene" is meant a gene encoding a polypeptide that is a serotonin-gated anion channel. In one embodiment, the mod-1 gene is from *C. elegans*.

By a "MOD-1 protein" or "MOD-1 polypeptide" is meant a polypeptide or fragment thereof, encoded by the mod-1 gene. In one embodiment, the MOD-1 protein or polypeptide is from *C. elegans*.

By "specifically binds" is meant an antibody that recognizes and binds to a serotonin-gated anion channel, but which does not substantially recognize and bind to other molecules in a sample, e.g., a biological sample that naturally includes other proteins.

By "mutant" is meant different from what normally appears, occurs, or functions. As used herein, the term refers to a nucleic acid sequence that is different from the wild-type sequence. This term also describes a protein encoded by the mutant nucleic acid sequence. The term also means an organism that contains a mutant nucleic acid sequence.

By "biological activity" is meant functional events mediated by a protein. In some embodiments, this includes events assayed by measuring the influx of ions into or out of a cell, or assaying the amount of serotonin binding to a channel. It also includes interactions of a polypeptide with another polypeptide. It also includes events that modify behavior or behavioral states. Such behavior includes, but is not limited to, movement, sexual behavior, or hallucinogenic behavior. Such behavioral states include, but are not limited to, migraine headaches, loss of appetite, gain of appetite, insomnia, inability to wake up, memory loss, nausea or vomiting, gastrointestinal cramps, ability or inability to learn, body temperature deregulation, moods, such as depression or mania, abnormal cardiovascular function, abnormal muscle contraction, and abnormal endocrine regulation.

As used herein, by "modulates" is meant increasing or decreasing the biological activity. Preferably the biological activity is increased or decreased 10% relative to a control. More preferably the biological activity is increased or decreased 50% relative to a control. Most preferably the biological activity is increased or decreased 90% relative to a control.

By "assaying" is meant analyzing the effect of a treatment or exposure, be it chemical or physical, administered to a whole animal or cells derived therefrom. The material being analyzed may be an animal, a cell, a lysate or extract derived from a cell, or a molecule derived from a cell. The analysis may be, for example, for the purpose of detecting current flow across a membrane, the rate of locomotion of an animal, altered gene expression, altered nucleic acid stability (e.g., mRNA stability), altered protein stability, altered protein levels, or altered protein biological activity. The means for analyzing may include, for example, recording current changes under voltage-clamp, voltage changes in current-clamp, or extracellular potentials, counting movements of an animal under a dissecting microscope, nucleic acid amplification techniques, reporter gene assays, antibody labeling, immunoprecipitation and phosphorylation assays, and other techniques known in the art for conducting the analyses of the invention.

By "neuron" is meant a cell of ectodermal embryonic origin derived from any part of the nervous system of an animal. Neurons express well-characterized neuron-specific markers that include neurofilament proteins, MAP2, and class III β-tubulin. Included as neurons are, for example, hippocampal, cortical, midbrain dopaminergic, motor, sensory, sympathetic, septal cholinergic, and cerebellar neurons.

As used herein, by "measuring" is meant assessing an anion channel activity. Measuring can be done by use of standard electrophysiology voltage-clamping or patch-clamping equipment.

By "condition" is meant a state of being or feeling. Conditions include, but are not limited to, migraine headaches, loss of appetite, gain of appetite, insomnia, inability to wake up, memory loss, nausea or vomiting, gastrointestinal cramps, ability or inability to learn, body temperature deregulation, moods, such as depression or mania, abnormal sexual or hallucinogenic behavior, abnormal cardiovascular function, abnormal muscle contraction, and abnormal endocrine regulation.

By "promoter" is meant a minimal sequence sufficient to direct transcription of an operably-linked gene.

By "operably linked" is meant that a gene and one or more regulatory sequences are connected in such a way as to permit gene expression when the appropriate molecules (e.g., transcriptional activator proteins) are bound to the regulatory sequences.

By "dominant-negative" is meant a nucleic acid sequence encoding a polypeptide which when expressed acts in a way to inhibit another polypeptide. This term also refers to the polypeptide itself. In one embodiment, the polypeptide that is inhibited is a wild-type polypeptide, and the dominant negative sequence encodes a mutant polypeptide of the same gene.

As referred to herein, by "constitutively active" is meant a nucleic acid sequence that encodes a polypeptide, which when expressed is in an active form at least as, or more often as the wild-type polypeptide is, in a cell in which wild-type polypeptide is naturally expressed. The polypeptide may be in an active form by being phosphorylated, or dephosphorylated, or cleaved from a propeptide to a peptide, or being ligand independent, or being mutated.

By "transgenic" is meant any cell or organism that includes a DNA sequence (transgene) that is inserted by artifice into a cell and becomes part of the genome of the organism that develops from that cell. As used herein, the transgenic organism is generally a transgenic non-human mammal (e.g., rodents such as rats or mice) or invertebrate (e.g., *Caenorhabditis elegans*).

By "antisense" is meant a nucleic acid sequence, regardless of length, that is complementary to the coding strand gene encoding a serotonin-gated anion channel. Preferably the antisense nucleic acid is capable of decreasing the activity of a serotonin-gated anion channel when present in a cell that normally is modulated by serotonin. Preferably the decrease is at least 10%, relative to a control, more preferably 25%, and most preferably 95%.

By "expose" is meant to allow contact between an animal, cell, lysate or extract derived from a cell, or molecule derived from a cell, and a test compound or activator of a serotonergic response.

By "characteristics" is meant properties or features. Characteristics include, but are not limited to, the nucleic acid sequence of a gene, or various alleles of a gene, the amino acid sequence of a protein, the level of expression of proteins or mRNA, and altered protein levels in tissues.

By "inhibit" is meant to decrease the level of expression of a serotonin-gated anion channel, or to decrease the function or activity of a serotonin-gated anion channel. Preferably the expression, function, or activity of the channel is deceased at least 25%, more preferably at least 50%, 70%, or 80%, and most preferably at least 95%, compared to a control (e.g., one which is not contacted with a test compound or an antisense nucleic acid).

BRIEF DESCRIPTION OF THE DRAWINGS

FIG. 1 shows the genomic sequence of *C. elegans* mod-1 (SEQ ID NO:

FIG. 2 shows the cDNA sequence encoding the *C. elegans* MOD-1 polypeptide (SEQ ID NO: 2).

FIG. 3 shows the *C. elegans* MOD-1 predicted amino acid sequence (SEQ ID NO: 3).

FIG. 6 shows the genomic sequence of the *C. elegans* mod-1 gene with the ok103 mutation (SEQ ID NO: 4).

FIG. 7 shows the genomic sequence of the *C. elegans* mod-1 gene with the n3034 mutation (SEQ ID NO: 5).

FIG. 8 shows the cDNA sequence of the *C. elegans* mod-1 gene with the n3034 mutation (SEQ ID NO: 6).

DETAILED DESCRIPTION OF THE INVENTION

Figure 4:
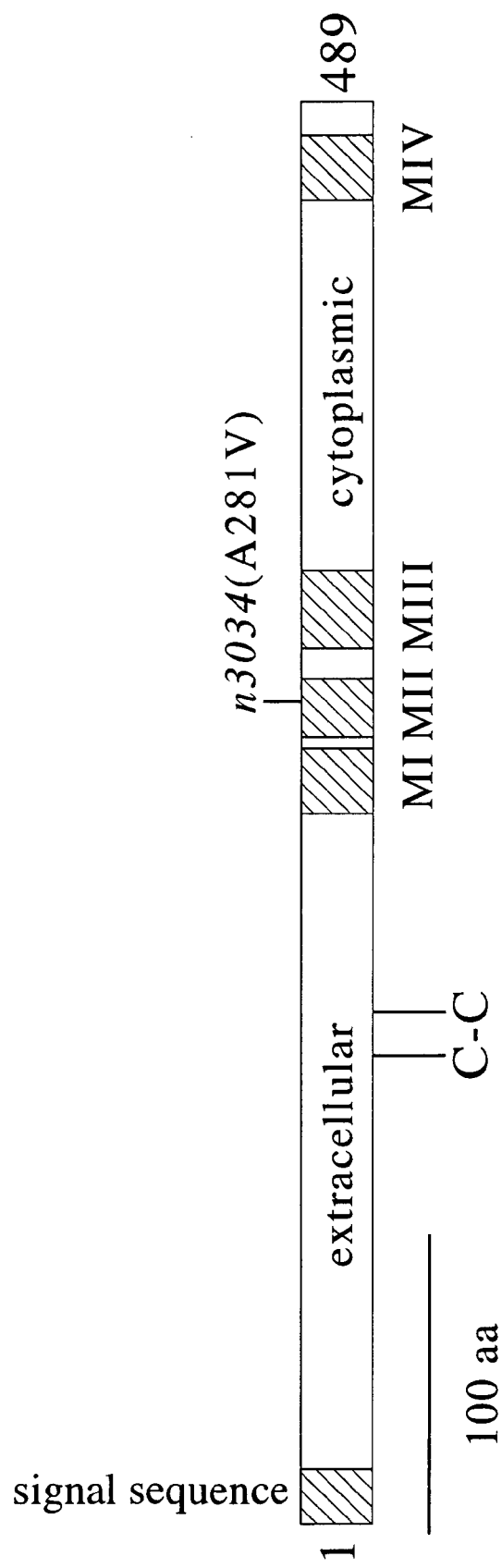
FIG. 4 shows the structure of the *C. elegans* MOD-1 amino acid sequence.

MOD-1 is Associated with Locomotion in C. elegans

Hermaphrodites respond to the presence of a bacterial lawn (their food source) by slowing their rate of locomotion. Animals deprived of bacteria for 30 minutes exhibit enhanced slowing when they encounter a bacterial lawn. Genetic, pharmacological, and laser ablation studies demonstrate that this modulatory response is mediated, in part, by serotonin.

Nematodes to be tested in the locomotion assay were picked as L4 animals 16–20 hours prior to the assay. Locomotion was assayed by placing the nematode on an assay plate (prepared by spreading a solution of E. coli strain HB101 on NGM agar in 5 cm plates, using a ring with an inner diameter of approximately 1 cm and an outer diameter of approximately 3.5 cm, and allowing the bacteria to grow 13–15 hours at 37° C.), observing each nematode under a dissecting microscope for 20 seconds, and counting the number of dorsal-ventral bends that occur in the anterior portion of the body during the interval.

For satiated animals, locomotion rate was assayed by removing five animals from plates with ample bacteria, washing them in S-basal buffer, and transferring them to the clear zone of the bacterial lawn of an assay plate using a capillary pipette. Beginning five minutes after transfer, the number of body bends was counted, as described above. This procedure was performed for each of the 5 animals.

To assay locomotion rates in food-deprived animals, 5–15 animals were removed from plates with ample food, washed twice in S-basal buffer, and transferred to 5 cm NGM agar plates without bacteria. Food-deprived animals were incubated on these plates for thirty minutes at room temperature, and then were transferred to assay plates. Locomotion was assayed, as described above for satiated animals.

The mod-1 mutants, obtained from the screen, as described above, exhibited a dominant phenotype of lack of decreased locomotion after being deprived of bacteria and then returned to a bacterial lawn.

MOD-1 is Associated with Locomotion Seen in C. elegans exposed to Serotonin

Animals to be tested for sensitivity or insensitivity to serotonin in this liquid locomotion assay were picked as L4 animals 16–20 hours prior to assay and the plates were coded so that the experimenter was blind to the genotype of the animals to be scored. On the day of the assay, serotonin (as a creatinine sulphate salt) was dissolved in M9 (at the required concentrations) just before use, and 200 μl were aliquoted to the wells of a flat-bottomed 96-well polystyrene plate. Twenty nematodes of each genotype to be tested were then transferred from the plate into a well containing liquid, using bacteria as glue. Care was taken not to hurt the animals while dislodging them from the pick, and the animals were observed immediately after transfer to ensure that all of them began to exhibit swimming motions. Then at various time intervals, the number of nematodes in each well that were still actively swimming was quantified.

Figure 5:
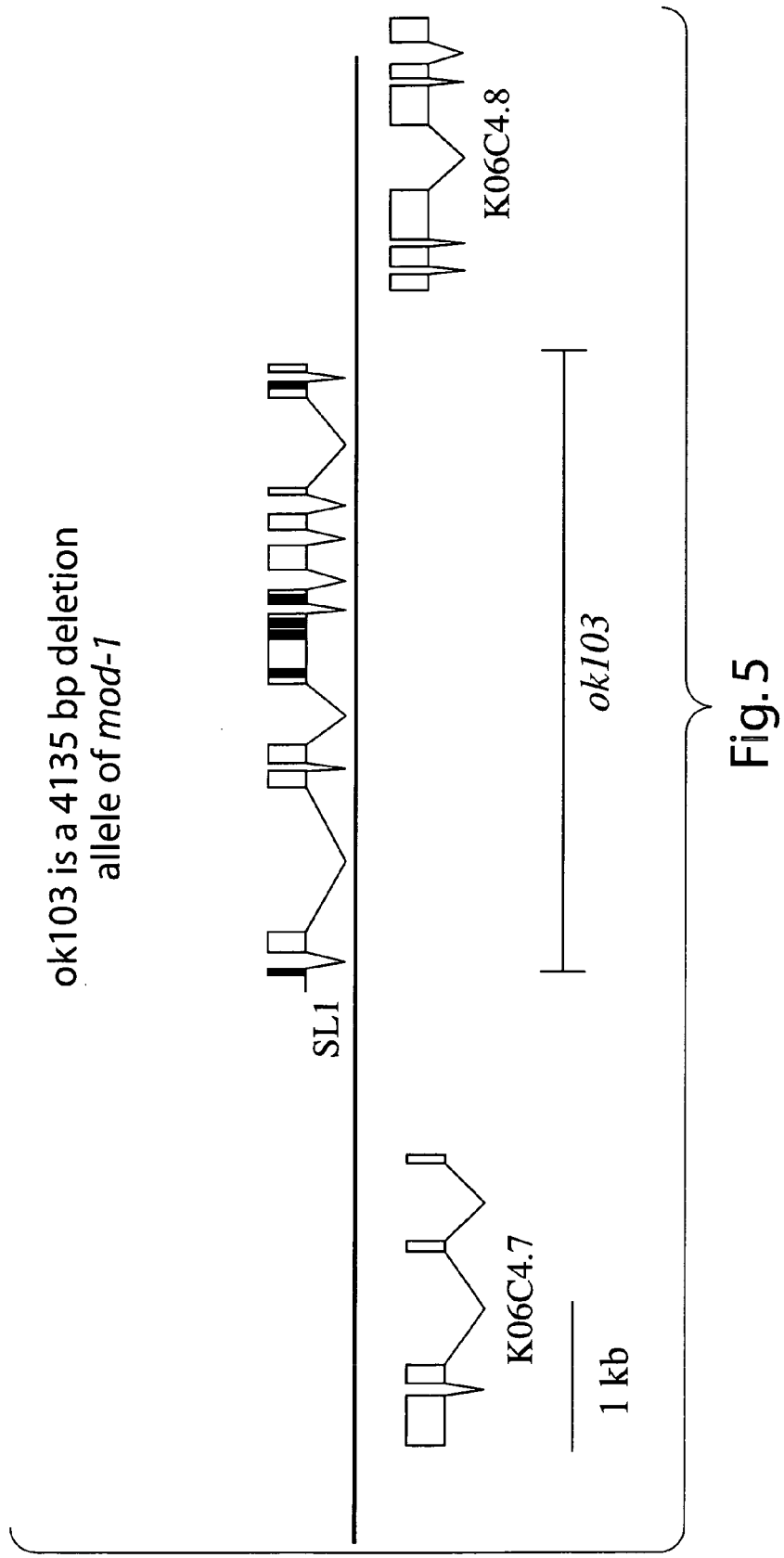
FIG. 5 is a map of the *C. elegans* strain carrying the ok103 mutation at the mod-1 locus. The ok103 mutation is a 4135 base pair deletion in the mod-1 genomic locus.

The mod-1 mutants, as described in the previous section, were further characterized using this technique. Animals carrying the n3034 mutation (FIG. 7 and FIG. 8) exhibited a dominant phenotype of insensitivity to exogenous serotonin in liquid locomotion assays. Animals carrying the ok103 mutation (FIG. 5 and FIG. 6) exhibited a recessive phenotype of insensitivity to exogenous serotonin in liquid locomotion assays.

The following examples are provided to illustrate the invention. These examples should not be construed as limiting.

EXAMPLE 1

Cloning of the mod-1 Gene

Both the wild type (FIG. 2), and mutant mod-1 cDNA have been obtained. The dominant serotonin resistance phenotype of animals carrying the mod-1(n3034) allele was used to genetically map mod-1(n3034) to a 0.7 map-unit interval on chromosome V. Deficiency analysis showed that the dominant serotonin resistance phenotype is not due to a haploinsufficiency of the mod-1 locus. The recessive nature of the serotonin resistance phenotype at early time points was exploited to perform standard transformation rescue experiments, and subsequently, the gene was cloned (FIG. 1).

EXAMPLE 2

MOD-1 Encodes a Ligand-Gated Ion Channel

The protein encoded by the mod-1 open reading frame responsible for the rescue is structurally similar to ligand-gated ion channels that belong to the nicotinic acetylcholine receptor (nAchR) family (FIG. 3 and FIG. 4). The nAchR family members are all pentameric channels with large N-terminal extracellular ligand-binding domains, four highly conserved transmembrane domains (M1–M4), and relatively divergent cytoplasmic domains between M3 and M4. nAchR family members include channels gated by acetylcholine, glycine, GABA, avermectin, and serotonin. Within the members of the nAchR family, structure-function analysis has been performed primarily on the acetylcholine receptor, but many structural and functional parallels have been seen with the other family members as well. In addition, chimeric channel studies show that there is a great deal of conservation at the functional level, even across the different ligand-gated members of the family. The M2 domains of the various subunits are predicted to line the pore of the channels. Site-directed mutagenesis studies of residues within this domain have demonstrated that ion specificity and modulation of the magnitude and frequency of current flux are determined, at least in part, by the residues that line the pore and those that are immediately adjacent to the pore on both the extracellular and cytoplasmic sides. Based on primary sequence analysis, MOD-1 appears to be equally divergent from all cloned nAchR family members.

EXAMPLE 3 mod-1 Forms a Serotonin-Gated Anion Channel

Figure 9A:
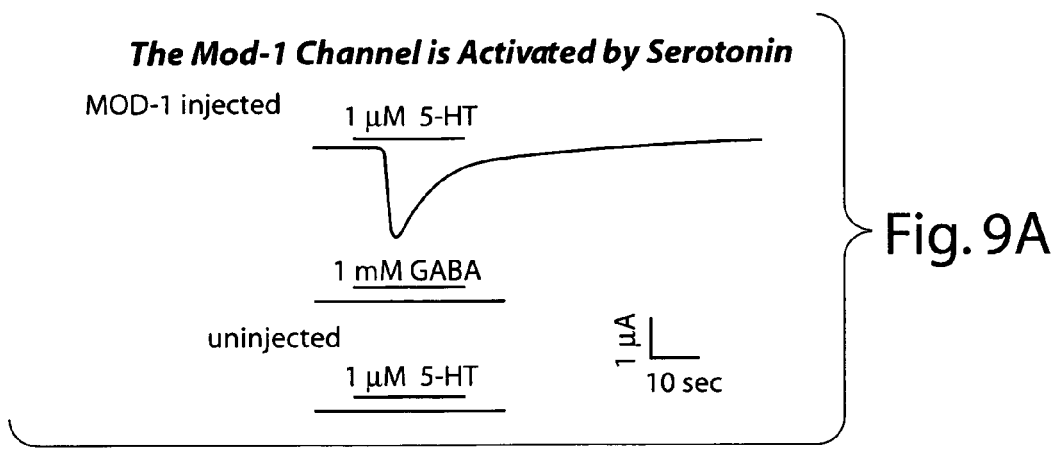
FIG. 9A is a time trace of the MOD-1 channel activated by serotonin.
Figure 9B:
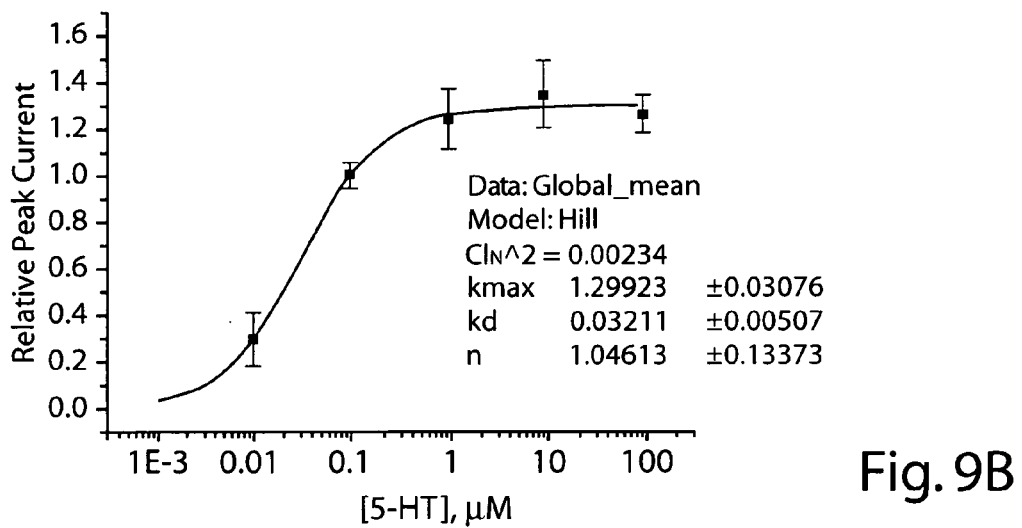
FIG. 9B is a graph illustrating a dose response curve of MOD-1 channel activity with respect to serotonin concentration.
Figure 9C:
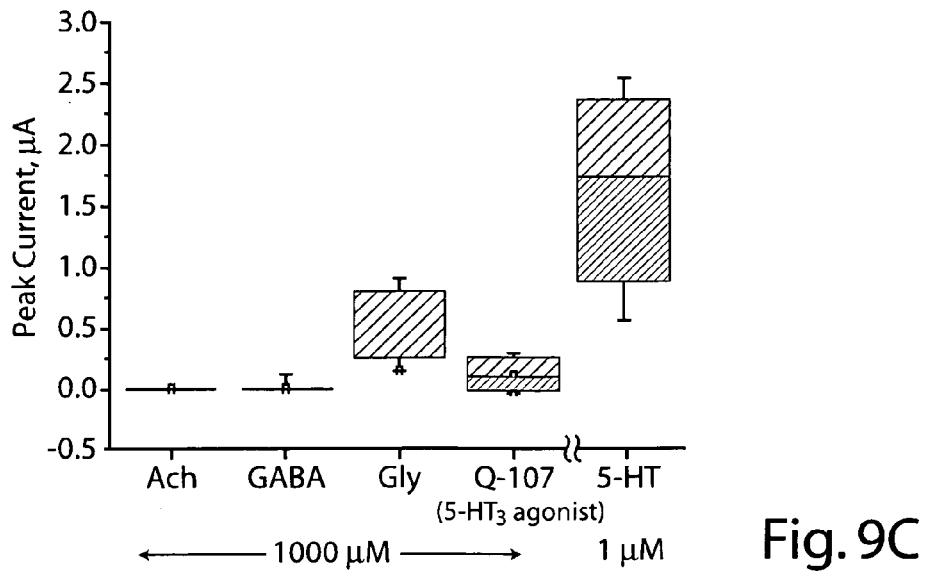
FIG. 9C is a graph illustrating the peak ionic current conducted by the MOD-1 channel in response to a variety of ligands, including acetylcholine, GABA, glycine, Q-107 (quipazine dimaleate, a 5-$HT_3$ receptor agonist), and serotonin.

MOD-1 was heterologously expressed in *Xenopus oocytes*, injected with 50 nl of *C. elegans* RNA, or MOD-1 was expressed in HEK cells transiently transfected by calcium phosphate precipitation. Forty-eight to 72 hours later, the cells or oocytes were screened under a voltage clamp (FIGS. 9A–9C). Application of 100 nM serotonin elicited large inward currents at a holding potential of −70 mV. Uninjected oocytes and nontransfected cells had no response to 10 μM serotonin. Application of 1 mM of other agonists of ligand-gated ion channels, such as acetylcholine, GABA, or glycine elicited little or no response from the MOD-1 channel.

Pretreatment of wild-type *C. elegans* with mianserin or methiothepin, serotonin receptor antagonists, prevents food-deprived animals from exhibiting the wild-type enhanced slowing response after they encounter bacteria. For this reason, even though both compounds have thus far been considered primarily to be antagonists of metabotropic serotonin receptors, we tested their abilities to affect MOD-1 in oocytes. The MOD-1 channel was inhibited by mianserin and methiothepin, with approximate $K_i$ values of 19 μM and 32 μM, respectively. Pre-treatment of mod-1 mutants with mianserin or methiothepin did not further affect the defective enhanced slowing response of these animals. These data indicate that mianserin and methiothepin interfere with the enhanced slowing response of *C. elegans* by antagonizing the MOD-1 serotonin-gated chloride channel.

EXAMPLE 4

MOD-1 is Permeable to Chloride Ions

Figure 10:
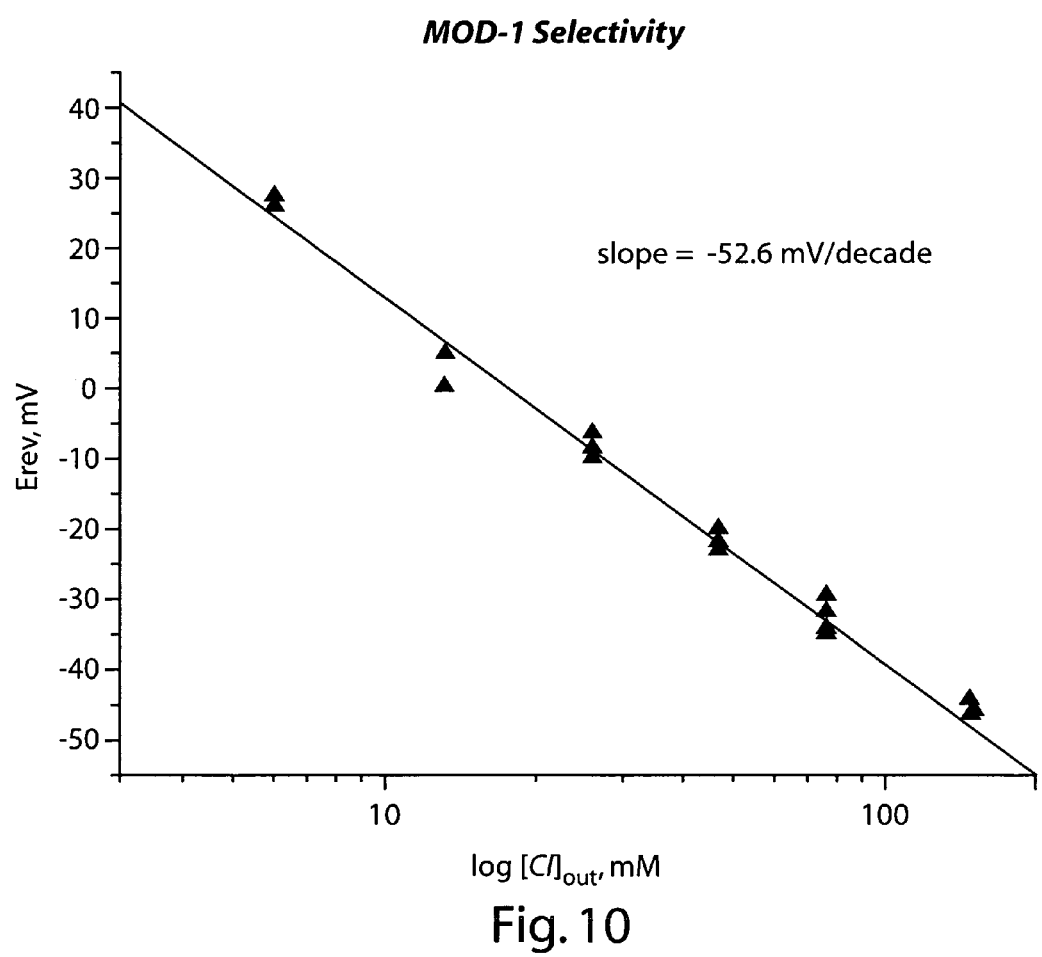
FIG. 10 is a graph illustrating the selectivity the MOD-1 channel has for chloride ions. As the concentration of chloride ions outside of the cell increases, the reversal potential becomes more negative.

Ion selectivity was determined by measuring changes in the reversal potential (voltage at which the serotonin response changes from an inward, negative, to an outward, positive, current) in response to varying the ionic composition of the bath solution. The reversal potential was insensitive to changes in cations ($Na^+$ or $K^+$), but shifted by approximately 50 mV for each 10-fold change in extracellular chloride concentration (FIG. 10).

EXAMPLE 5

Antibodies to MOD-1

Using MOD-1 polypeptides described herein, anti-MOD-1 antibodies were produced using standard techniques. Peptides to either the putative N-terminal extracellular domain, or to a putative C-terminal intracellular domain, located between transmembrane-spanning regions III and IV, were synthesized, and coupled to GST using standard techniques. The peptides were used to immunize two different rabbits and three different rats. The antibodies were then affinity purified on a HIS-tagged-MOD-1 affinity column using standard techniques, and were shown to specifically identify GST-MOD-1, by Western blot techniques.

Polypeptides for additional antibody production may be produced by recombinant or synthetic peptide techniques (see, e.g., Solid Phase Peptide Synthesis, 2nd ed., 1984 The Pierce Chemical Co., Rockford, Ill.; Ausubel et al., supra).

Alternatively, monoclonal antibodies may be prepared using a serotonin-gated anion channel polypeptide (or immunogenic fragment or analog) and standard hybridoma technology (see, e.g., Kohler et al., Nature 256:495, 1975; Kohler et al., Eur. J. Immunol. 6:511, 1976; Kohler et al., Eur. J. Immunol. 6:292, 1976; Hammerling et al., *In Monoclonal Antibodies and T Cell Hybridomas*, Elsevier, N.Y., 1981; Ausubel et al., supra).

Once produced, polyclonal or monoclonal antibodies are tested for specific recognition by Western blot or immunoprecipitation analysis (by the methods described in Ausubel et al., supra). Antibodies that specifically recognize a serotonin-gated anion channel polypeptide, as described herein, are considered to be useful in the invention. Anti-serotonin-gated anion channel antibodies, as isolated above, may be used, e.g., in an immunoassay to assay or monitor the level of a serotonin-gated anion channel polypeptide produced by *C. elegans* or a mammal, or to screen for compounds that modulate serotonin-gated anion channel polypeptide production. Anti-serotonin-gated anion channel antibodies may also be used to identify cells that express a serotonin-gated anion channel gene.

EXAMPLE 6

Cloning of Mammalian Serotonin-Gated Chloride Channels with Biophysical Properties Similar to the *C. elegans* Serotonin-Gated Anion Channel Based on our isolation of a novel nematode mod-1 cDNA, the isolation of mammalian nucleic acid sequences encoding a serotonin-gated anion channel, including human sequences, is made possible using the strategies described herein and standard techniques.

I. Expression Cloning Using Xenopus Oocytes

A. Poly(A)+ RNA isolated from various tissues types is injected into *Xenopus oocytes*. Initial screening is performed on total Poly(A)+ RNA from human brain, human spinal cord, human testes, rat brain, rat testes, mouse brain, and mouse testes.

B. Functional expression of serotonin-gated ion channels is assayed by measuring ion current in voltage-clamped oocytes elicited by application of serotonin at a concentration of 100 nM or less. Several strategies can be used to identify those serotonin-gated currents that are likely to be conducted by an anion-selective ionotropic channel, comparable to MOD-1.

1) High affinity for serotonin. We have found that MOD-1 channels are activated by lower concentrations of serotonin than $5\text{-HT}_{3a}$ type serotonin receptors. MOD-1 has a half-maximal response with 50 nM serotonin. For $5\text{-HT}_{3a}$ channels, no response is detectable in 1 μM serotonin, but 10 μM serotonin elicits a robust current. The lower affinity of the $5\text{-HT}_{3a}$ receptor for serotonin is also reflected in its faster and more complete "washout" (reduction of current back to baseline when the drug is washed off) compared to MOD-1. Serotonin-gated anion channels that have a lower affinity for serotonin can also be isolated using the methods, as described above.

2) Shifts in the reversal potential caused by changes in $[Cl]_o$. In standard external saline (140 mM NaCl, 2 mM $CaCl_2$, 1 mM $MgCl_2$, 2.5 mM glucose, and 10 mM HEPES) the reversal potential ($E_{rev}$) for MOD-1 is about −20 mV, whereas the $5\text{-HT}_{3a}$ current reverses at about 0 mV. Decreasing the extracellular $Cl^-$ to 50 mM by substitution with gluconate, while keeping the cation concentration fixed, will cause $E_{rev}$ of the MOD-1 current to shift to >+15 mV whereas $E_{rev}$, for the 5-HT$_{3a}$ current will not be changed.

3) Exclusion of metabotropic (second messenger dependent) serotonin-gated currents. Ligand binding to metabotropic 5-HT receptors, such as the 5-HT$_{IC}$, receptor, expressed in *Xenopus* oocytes elicits a large Cl⁻ current due to IP$_3$-triggered release of intracellular Ca$^{2+}$ and subsequent activation of endogenous Ca$^{2+}$-activated Cl⁻ channels. This signaling pathway can be suppressed by direct injection of IP$_3$, which exhausts the stores of releasable Ca$^{2+}$ and thereby causes the oocyte to be refractory to metabotropic 5-HT receptor responses that depend on internal Ca$^{2+}$ release. Serotonin-gated responses acting through second messenger systems also differ from ionotropic responses in that second-messenger based systems often give rise to oscillations in ion current. These oscillations arise from the dynamic aspects of intracellular Ca$^{2+}$ regulation. In contrast, current conducted by ionotropic receptors always have a monophasic time course.

4) 5-HT$_{3a}$ specific toxin. The 41-amino acid snail venom σ-conotoxin GVIIIA is a potent competitive antagonist of the 5-HT$_{3a}$ channel (IC 50 on the order of 50 nM). One can test whether MOD-1, like all other known 5-HT class receptors, is insensitive to µM concentrations of this conotoxin. This strategy may provide a simple method for eliminating the only other known serotonin-gated ionotropic receptors (5-HT$_3$, and 5-HT$_{3b}$).

5) Suppression of all known forms of serotonin channels. Ideally, expression cloning of mammalian serotonin-gated chloride channels is achieved under conditions in which all other known serotonin gated channels and receptors are blocked. The blockage of these serotonin gated channels and receptors can be accomplished by bathing the oocyte in compounds that inhibit their function. For example, the oocytes may be bathed in a solution containing the calcium chelator BAPTA-AM. The concentration of BAPTA-AM in the bath is approximately 200 µM. While BAPTA-AM blocks other known serotonin gated receptors, it does not affect the function of MOD-1.

Alternatively, the bath may contain a high concentration of calcium, for example, approximately 10 mM, that is sufficient to block serotonin gated cation channels, but does not block MOD-1. In another method, serotonin gated Na⁺/K⁺ channels may be blocked using, for example, choline chloride or N-methyl glucamine. In other methods, the bath may contain, specific serotonin antagonists. For example, granisetron or ondansetron (at approximately 1 µM concentrations) may be used to inhibit the serotonin-gated cation channel.

One skilled in the art can appreciate that a combination of these methods may provide the maximal blockage of all known serotonin gated ion channels and receptors. For example, one preferred combination of serotonin gated channel and receptor blockers is BAPTA-AM and/or choline chloride or N-methyl-glucamine.

Figure 11:
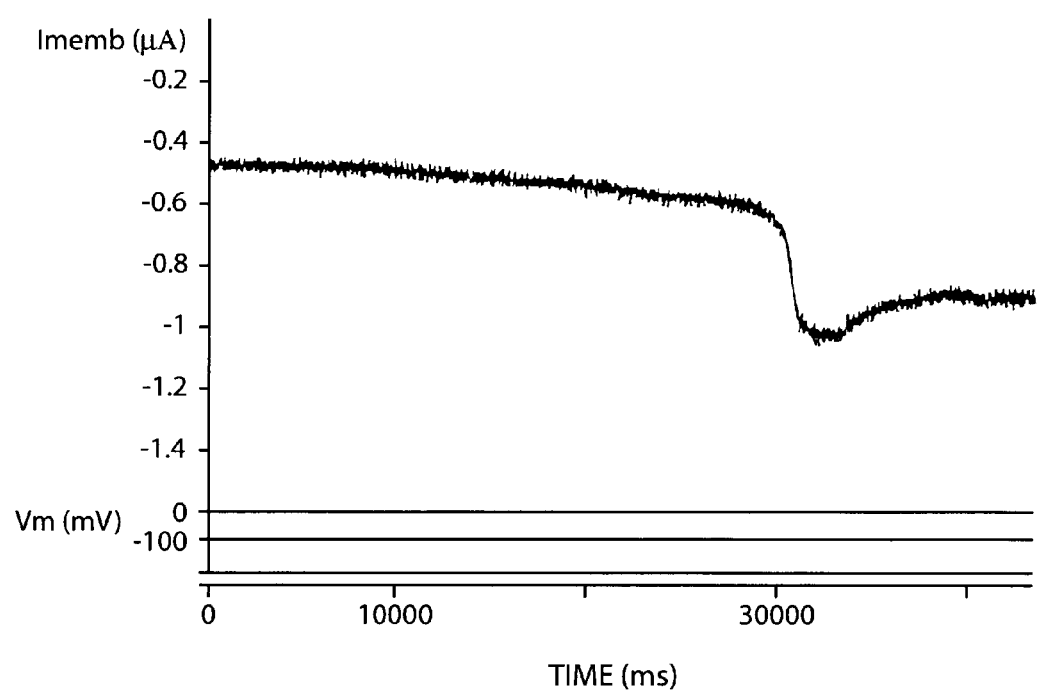
FIG. 11 is a time trace of a MOD-1-like response from rat brain RNA.

A method to identify a mammalian serotonin-gated chloride channel was carried out essentially as described above. Oocytes were injected with rat cortex RNA. Six days later, the oocytes were bathed in BAPTA-AM (200 µM) for 2 hours at room temperature, to deplete internal Ca$^{++}$ stores, thereby preventing G-protein-coupled serotonin receptors from having an effect through calcium-dependent second messenger pathways. The oocytes were then screened under a voltage clamp, in a buffer containing 96 mM NaCl, 2 mM KCl, 0.3 mM CaCl$_2$, 1 mM MgCl$_2$, and 5 mM HEPES (pH 7.5), and with 100 mM Tris added. Addition of Tris completely blocks the 5-HT$_3$ cation channel. Application of 1 µM serotonin for 1 minute elicited inward currents at a holding potential of −70 mV in about 10% of the oocytes (FIG. 11).

These results indicate that rat brain RNA elicits a MOD-1-like serotonin-activated current from oocytes. This current is not a 5-HT$_3$, (and is very unlikely to be another permeant 5-HT ionotropic cation channel receptor) or a G-protein-coupled serotonin receptor-activated current. The isolation of the specific RNA that mediates these results is achieved, as described below.

Figure 12:
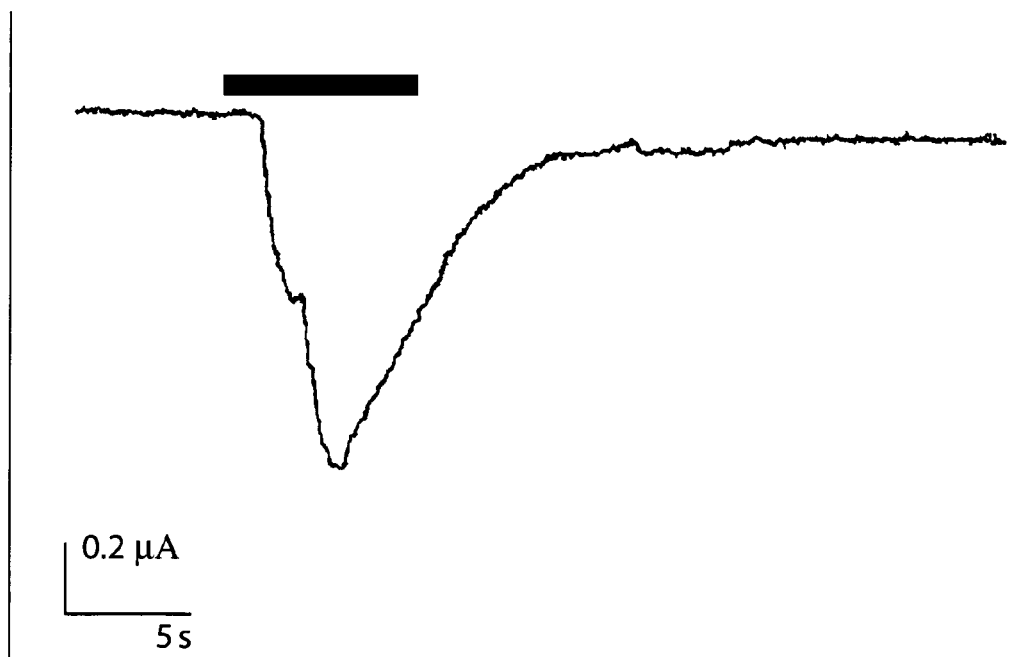
FIG. 12 is a time trace of a MOD-1-like response of an oocyte injected with rat cortex RNA.

In additional studies, oocytes were injected with poly(A)+ RNA from rat cortex, striatum, or thalamus, as described above. The oocytes were bathed in 200 µM BAPTA-AM for 2 hours, and were then screened under a voltage clamp, in a bath solution containing 2 mM Co$^{2+}$ to block 5-HT$_{3a}$ responses. Application of 1 µM serotonin elicited inward currents at a holding potential of −70 mV in approximately 33% of the oocytes. FIG. 12 is a representative time trace of a MOD-1-like response from an oocytes injected with rat cortex RNA. These MOD-1-like currents were not detected in oocytes injected with rat RNA from spinal cord, heart, lung, or testes.

C. When a response that fits some or all of the criteria outlined above has been identified, one can size fractionate the RNA as the first step toward isolating a specific RNA (and corresponding cDNA). Our preliminary studies of MOD-1 and data from the cloning of the 5-HT$_{3a}$ cation channel demonstrate that functional serotonin-gated channels can be formed by homomultimers of a single gene product. This result tremendously improves the feasibility of the expression-cloning strategy. A single RNA species is capable of coding for a functional ionotropic channel, which implies that RNA size fractionation should not cause a loss of serotonin response, as might occur with a heteromultimeric channel protein. Sucrose gradients are used to size fractionate total RNA and individual fractions are injected into oocytes to test for serotonin-gated responses. Once a small enough pool has been determined by such methods, the RNA from that pool is used to prepare cDNA libraries in appropriate vectors. Resulting clones are end-sequenced, and RNA is synthesized from distinct clones and tested in oocytes for the required activity. Clones that produce the desired response are then sequenced in their entirety.

If the results from these experiments indicate that the mammalian serotonin-gated anion channel consists of a heteromultimer rather than a homomultimer, then various pools of mammalian RNA are injected into the oocyte along with any RNAs encoding putative serotonin-gated anion channels. The functional expression of serotonin-gated anion channels can be assayed, as described above. When a pool meets the requirements of contributing to the make-up of a serotonin-gated anion channel, as outlined above, the pool can be further fractionated, and the assays, as described above, are repeated. The methods used to identify and clone the heteromultimers of the serotonin-gated anion channel then proceed, as described above.

Alternatively, a cDNA library, for example, a human or rat brain cDNA library can be functionally screened to identify and clone mammalian serotonin-gated chloride channels. To this effect, a rat brain cDNA library, containing 10$^9$ plaque forming units from greater than 10$^7$ clones with insert sizes of 1.3 to 2.5 kb that have been directionally cloned into the expression vector cmvSPORT, was purchased (Gibco). The library was divided into 20 plates. Colonies were pooled from within one plate, and DNA plasmids were isolated and linearized using restriction enzymes. RNA was then synthesized, using standard methods.

Oocytes are injected with the synthesized RNA (50–100 ng) and responses to serotonin, in the presence of BAPTA-AM and 2 mM $Co^{2+}$ are recorded. As a control for the quality of the library and RNA synthesis, serotonin was applied to oocytes not exposed to the BAPTA-AM. Large oscillatory currents were observed. Such responses are typical of metabotropic serotonin receptors, and indicate that the quality of the library and the RNA synthesis is good.

II. Electrophysiological Screening of Endogenous Serotonin-Gated Currents

If the above expression-cloning strategy is not successful, or in the alternative, one can identify MOD-1 like serotonin-gated responses in mammalian cells. Both acutely dissociated neurons and brain-derived cell lines may be screened. Once a cell type with a robust serotonin-gated, ionotropic, anion-selective current is identified, these cells are used as an enriched source from which to isolate mRNA coding for a MOD-1-like receptor. Poly(A)+ RNA is then prepared from the positive tissue or cell line, and the same strategy as the one outlined in I is used to identify the clone(s) responsible for the response.

III. Other Approaches

In addition to the expression cloning strategies outlined above in sections I and II, complementary approaches can be taken to identify mammalian serotonin-gated chloride channels.

A. EST databases are be systematically combed for sequences with similarities to the mod-1 cDNA or protein sequence. This process is greatly enhanced by the identification of regions of the MOD-1 protein that allow it to be gated specifically by serotonin, and the regions of the protein that are predicted to be important for allowing anions to pass freely through the channel pore. Existing search algorithms for transmembrane topology (MEMSAT, TMAP, PHDtopology), protein fold motifs (TOPITS, UCLA-DOE Structure Prediction Server), and three-dimensional structures (SCOP) are used to search for sequences that may be clear candidates for mammalian homologs of MOD-1. Full-length cDNAs for such candidates are obtained and tested in the above-described oocyte expression system for the desired response.

B. Hybridization techniques are used to clone additional serotonin-gated anion channels. These techniques are well known to those skilled in the art, and are described, for example, in Ausubel et al., Current Protocols in Molecular Biology, John Wiley & Sons, New York, N.Y., 1990, and *Guide to Molecular Cloning Techniques,* 1987, S. L. Berger and A. R. Kimmel, eds., Academic Press, New York. If desired, a combination of different oligonucleotide probes may be used for the screening of a recombinant DNA library. The oligonucleotides are, for example, labeled with $^{32}P$ using methods known in the art, and the detectably-labeled oligonucleotides are used to probe filter replicas from a recombinant DNA library. Recombinant DNA libraries (for example, human cDNA libraries, such as brain or testes-derived cDNA libraries) are prepared according to methods well known in the art, for example, as described in Ausubel et al., supra, or are obtained from commercial sources.

For detection or isolation of closely related serotonin-gated anion channel sequences, high stringency hybridization conditions are employed; such conditions include hybridization at about 42° C. and about 50% formamide; a first wash at about 65° C., about 2×SSC, and 1% SDS; followed by a second wash at about 65° C. and about 0.1% SDS, 1×SSC. Lower stringency conditions for detecting a gene encoding a serotonin-gated anion channel having less sequence identity to the nematode mod-1 gene described herein include, for example, hybridization at about 42° C. in the absence of formamide; a first wash at about 42° C., about 6×SSC, and about 1% SDS; and a second wash at about 50° C., about 6×SSC, and about 1% SDS C. Oligonucleotides that partially encode, or are complementary to nucleic acids encoding serotonin-gated anion channel-specific oligonucleotides are used as primers in PCR cloning strategies. Such PCR methods are well known in the art and are described, for example, in *PCR Technology,* H. A. Erlich, ed., Stockton Press, London, 1989; *PCR Protocols: A Guide to Methods and Applications,* M. A. Innis, D. H. Gelfand, J. J. Sninsky, and T. J. White, eds., Academic Press, Inc., New York, 1990; and Ausubel et al., supra. Again, sequences corresponding to sequences thought to encode amino acids important for serotonin-gated anion channel structure or function are preferred for use in isolating other sequences structurally and/or functionally related to a serotonin-gated anion channel. Such sequences are used to screen cDNA, as well as genomic DNA libraries. The sequences also include those that are not known to be important for serotonin-gated anion channel structure or function.

D. Once full-length clones are isolated from the appropriate cDNA library, they are tested in the oocyte, or other suitable cell, for the desired response. The PCR and hybridization cloning strategies, as described above, are enhanced by knowledge of regions of the MOD-1 protein capable of binding serotonin and/or conducting chloride ions. The strategies, however, can be used even without identification of regions of the MOD-1 protein capable of binding serotonin and/or conducting chloride ions.

E. Receptors for small ligands have been found using assays for ligand-binding. Serotonin is immobilized to a solid-support using a linker, and established mammalian cell lines and cells injected with cDNA pools from various tissue sources are assayed for binding to serotonin. Cells that bind are isolated and the cDNA from within the cell is isolated using single-cell PCR. This step can be used as an enrichment step before proceeding with strategies outlined in section I. The cDNA clones are sequenced and those that fit the general protein topology constraints for ligand-gated ion channels are tested for the serotonin-gated anion channel-like characteristics in the ooctye system, or other suitable systems.

E. An antibody to MOD-1 can also be used to detect cross-reacting mammalian proteins. This can be done by co-immunoprecipitations, using the MOD-1 antibody, and standard techniques.

EXAMPLE 7

Screening Systems for Identifying Therapeutics

Based on our experimental results, we have developed a number of screening procedures for identifying therapeutic compounds (e.g., pharmaceuticals to treat disorders associated with serotonin-mediated cellular responses), or leads for such compounds, that can be used in human patients. In particular examples, compounds that specifically down-regulate or specifically increase serotonin-gated anion channel biological activity or the biological activity of their human homologs are considered useful in the invention.

Also useful in the invention, are compounds that specifically affect other serotonin receptors and a serotonin-gated anion channel, or other serotonin receptors, but specifically not a serotonin-gated anion channel. In general, the screening methods of the invention involve screening any number of compounds for therapeutically active agents by employing any number of in vitro or in vivo experimental systems. Exemplary methods useful for the identification of such compounds are detailed below.

The methods of the invention simplify the evaluation, identification, and development of active agents for the treatment of conditions associated with serotonin-mediated cellular responses, such as depression, panic disorders, obsessive compulsive disorder, sleep disorders, eating disorders, nausea and vomiting, other gastrointestinal disorders, and migraines, and the side-effects associated with these drugs. In general, the screening methods provide a facile means for selecting natural or synthetic product extracts or compounds of interest from a large population. These candidates are further evaluated and condensed to a few active and selective materials. Constituents of this pool are then purified and evaluated using methods described herein, to determine their ability to modulate serotonin-mediated responses and conditions.

Below we describe screening methods for evaluating the efficacy of a compound for use in the treatment of diseases associated with serotonin-mediated neurotransmission.

Test Extracts and Compounds

In general, novel drugs for the treatment of serotonin-mediated cellular responses and conditions are identified from large libraries of both natural product, or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modifications of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including, but not limited to, Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by combinatorial-chemistry methods or standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their effects on compounds associated with serotonin-mediated cellular responses should be employed whenever possible.

When a crude extract is found to affect serotonin-mediated responses or conditions, further fractionation of the positive lead extract is necessary to isolate chemical constituents responsible for the observed effect. Thus, the goal of the extraction, fractionation, and purification process is the careful characterization and identification of a chemical entity within the crude extract having activities that affect serotonin-mediated cellular responses. The same in vivo and in vitro assays described herein for the detection of activities in mixtures of compounds can be used to purify the active component and to test derivatives thereof. Methods of fractionation and purification of such heterogenous extracts are known in the art. If desired, compounds shown to be useful agents for the treatment of pathogenicity are chemically modified according to methods known in the art. Compounds identified as being of therapeutic value are subsequently analyzed using any standard animal model of serotonin-mediated cellular responses known in the art.

There now follow examples of systems useful for evaluating the efficacy of a molecule or compound in treating (or preventing) a condition associated with serotonin-mediated cellular responses, and the side-effects resulting from the treatment of these conditions.

Assays to be used for identifying compounds that affect serotonin-mediated cellular responses include assaying locomotion rates of nematodes exposed to test compounds. It also includes adding a test compound to a cell and assaying serotonin-gated anion channel expression at the nucleic acid level or at the polypeptide level. The changes in serotonin-gated anion channel RNA levels can be monitored by Northern blot analysis, or by highly sensitive quantitative RT-PCR assays. The changes in the levels of serotonin-gated anion channel polypeptide can be monitored through the use of antibodies, including standard Western blot analysis, and immunohistochemistry.

The invention also includes assays that measure ionic current through a channel as a means of identifying a compound that affects serotonin-mediated cellular responses. In the presence of an agonist, the serotonin-gated anion channel is likely to be activated, and this will lead to an increase in the current carried through the channel. This change in current flow can be measured using standard electrophysiological methods. In the presence of an antagonist, the serotonin-gated anion channel is likely to be refractory to the application of serotonin, and less, or no current will pass through the channel. Such changes can be measured using standard electrophysiological methods.

The invention also includes assays that measure the concentration of serotonin, or a test compound required to activate a serotonin-gated anion channel, as compared to the 5-$HT_3$ receptor. In both HEK cell and Xenopus oocyte expression systems, serotonin-gated currents are detectable at lower concentration of agonist (10–50 nM) for MOD-1 receptors than for 5-$HT_3$ receptors (>10 μM). This observation provides a tool for exploring the basis of dose-dependent clinical responses. Effects produced by low-dose serotonin or test compounds may be mediated by serotonin-gated anion channels, while effects at 100-fold higher serotonin or test compound concentrations are likely to arise from a combination of serotonin-gated anion channels and 5-$HT_3$ type receptor activation.

EXAMPLE 8

Diagnostic Probes cDNA fragments can be used as hybridization probes for allelic markers for haplotype analysis of human disorders or conditions linked to the locus of a serotonin-gated anion channel locus. Such analyses can also be performed using other standard techniques, such as PCR.

EXAMPLE 9

Pharmacogenetics of Responses to Therapeutics for Serotonin-Mediated Conditions

A serotonin-gated anion channel can serve as a marker for determining how an individual might respond to a given therapeutic for a serotonin-mediated condition. Genetic analysis of an individual's serotonin-gated anion channel locus can be completed as described above. Once a group of major mutant alleles has been established, PCR based genotyping assays can be developed to make a molecular diagnosis of an abnormal serotonin-gated anion channel. When information regarding how individuals with a specific serotonin-gated anion channel allele respond to particular therapies is combined with molecular diagnosis techniques, it is feasible to select an optimal therapy to treat serotonin-mediated conditions.

EXAMPLE 10

Therapies that Modulate Conditions Mediated by Serotonergic pathways: Effect of Serotonin-Gated Anion Channel Genotype Patients experiencing a specific condition, or set of conditions, mediated by serotonin are placed into one of four treatment groups: placebo or 3 increasing doses of a given drug. During and at the end of the treatment period, the patients are evaluated for the effect of the drug on modulation of the condition(s). The patients are also evaluated for side-effects experienced as a result of drug administration. Patients are also characterized for the presence of various alleles of a serotonin-gated anion channel, and optionally, other serotonin-mediated receptor alleles and/or their respective protein levels. Results of these studies can be correlated to design therapies that provide optimal relief from the serotonin-mediated condition(s), with the fewest side-effects, in a patient with a specific serotonin-gated anion channel allele, or particular protein levels. In addition, other known serotonin-mediated receptors may be characterized and included in the development of the therapeutic protocol.

The patients can also be genotyped for polymorphisms in specific enzymes required for the metabolism of a given therapeutic used in the treatment of serotonin-mediated conditions. Such enzymes to be assessed include thiopurine S-methyltransferase (TPMT), dihydropyrimidine dehydrogenase (DPD), aldehyde dehydrogenase (ALDH), glutathione S-transferase (GST), uridine diphosphate glucuronosyl-transferase (UGTs), and cytochrome P450 enzymes. Once knowledge of an individual's drug metabolism profile is obtained, therapies to treat serotonin-mediated conditions can be more optimally designed to provide maximal efficacy with minimal side-effects.

Antisense RNA

1. Design of antisense systems. One way in which antisense RNA can be synthesized is through a system. One example of a system includes, but is not limited to a complete panel of adenovirus constructs. The panel may consist of approximately four types of recombinant virus: A) A sense orientation virus for each serotonin-gated anion channel open reading frame; these viruses are designed to massively overexpress the recombinant protein in infected cells. B) Antisense orientation viruses in which the viral promoter drives the synthesis of an mRNA of opposite polarity to the serotonin-gated anion channel RNA, thereby shutting off host cell synthesis of the targeted protein coding region. C) Sub-domain expression viruses; these constructs express only a partial serotonin-gated anion channel protein in infected cells. D) Control viruses; functional analysis of serotonin-gated anion channel requires suitable positive and negative controls for comparison.

2. Confirmation of recombinant adenovirus function. Verification of the sense adenovirus function involves infection of tissue culture cells and determination of protein expression levels. This can be done by Western blot analysis. Functional analysis of the antisense viruses may be done at the RNA level using either Northern blots of total RNA harvested from infected tissue culture cells or ribonuclease protection assays. Western blot analysis of infected cells may be used to determine whether the expressed antisense RNA interferes with serotonin-gated anion channel expression in the host cell.

3. Documentation that serotonin-gated anion channel over-expression results in increased serotonin-gated anion channel activity. Determination of whether serotonin-gated anion channel over-expression results in increased serotonin-gated channel activity can be done by measuring the ionic current across a membrane elicited by serotonin using standard voltage-clamping techniques. The surface area of the membrane to be analyzed is pre-determined and remains constant for assaying both over-expressing and control samples.

4. Documentation that antisense serotonin-gated anion channel over-expression results in decreased serotonin-gated anion channel activity. Having confirmed that serotonin-gated anion channel over-expression renders cells more likely to exhibit increased serotonin-gated anion channel activity, one may examine whether the antisense adenoviruses render the same cells resistant to the channel activity, using the above-described methods.

5. Identification of antisense oligonucleotides. Concomitant to the adenovirus work, a series of antisense oligonucleotides to various regions of a serotonin-gated anion channel can also be designed. A generally-accepted model of how antisense oligonucleotides function proposes that the formation of RNA/DNA duplexes in the nucleus activates cellular RNase H enzymes which enzymatically degrade the mRNA component of the hybrid. Virtually any region of the mRNA can be targeted, and therefore choosing an appropriate sequence to target is somewhat empirical. One site frequently targeted is the translation initiation site. Alternatively, one can design antisense oligonucleotides that systematically "walk" down a nucleic acid sequence of interest. Many factors, including secondary structure of the target mRNA and the binding affinity of the targeted sequence determine whether a particular oligonucleotide will be effective, necessitating several oligos for a serotonin-gated anion channel. Oligonucleotides to serotonin-gated anion channel mRNA can be made based on the available computer algorithms for predicting binding affinities and mRNA secondary structures. These and other oligonucleotides may be tested for their ability to target their respective mRNAs for degradation using Northern blot analysis.

6. Optimization of oligonucleotides. A secondary round of oligonucleotides may be made when effective target regions have been identified. These oligonucleotides target sequences in the immediate vicinity of the most active antisense oligonucleotides identified using methods such as those provided above. A second round of testing by Northern blot analysis may be required.

7. Testing antisense oligonucleotides in vitro. Following successful identification and optimization of targeting oligonucleotides, one may test these antisense oligonucleotides in tissue culture cells. Experimental procedures may parallel those used in the recombinant antisense adenovirus work. Negative control oligonucleotides with mismatch sequences are used to establish baseline or non-specific effects. Assisted transfection of the oligonucleotides using, for example, cation lipid carriers may be compared to unassisted transfection. Confirmation of the effectiveness of specific antisense oligonucleotides prompts synthesis of oligonucleotides with modified phosphodiester linkages, such as phosphorothioate or methylimino substituted oligos. These modified oligonucleotides may also be tested in vitro.

Another therapeutic approach within this invention involves administration of recombinant protein fragments or antibodies to a serotonin-gated anion channel, either directly to the site where modulation of serotonin transmission is desirable (for example, by injection) or by systemic administration (for example, by any conventional recombinant protein administration technique).

The dosage of serotonin-gated anion channel, the serotonin-gated anion channel fragment, serotonin-gated anion channel mutant protein, or antibody to a serotonin-gated anion channel depends on a number of factors, including the size and health of the individual patient, but, generally, between 0.1 mg and 100 mg inclusive are administered per day to an adult in any pharmaceutically acceptable formulation.

Administration

A serotonin-gated anion channel mutant protein or protein fragment, gene encoding the same, gene encoding a serotonin-gated anion channel antisense RNA, or modulator of a serotonin-gated anion channel may be administered within a pharmaceutically-acceptable diluent, carrier, or excipient, in unit dosage form. Conventional pharmaceutical practice may be employed to provide suitable formulations or compositions to administer the compounds to patients suffering from a disease or condition associated with the serotonergic pathway. Administration may begin before the patient is symptomatic. Any appropriate route of administration may be employed, for example, administration may be parenteral, intravenous, intraarterial, subcutaneous, intramuscular, intracranial, intraorbital, ophthalmic, intraventricular, intracapsular, intraspinal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington's Pharmaceutical Sciences," (Remington: The Science and Practice of Pharmacy, 19$^{th}$ ed., A. R. Gennaro, ed., Mack Publishing Co., Easton, Pa., 1995). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for serotonin-gated anion channel modulatory compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, treatment with serotonin-gated anion channel mutant proteins or serotonin-gated anion channel fragments, related genes, or other modulatory compounds may be combined with more traditional therapies for therapies associated with serotonin-mediated cellular responses.

EXAMPLE 11

Transgenic Mice

Transgenic mouse expression vectors, including neuronal, testes, and smooth muscle cell-specific promoter constructs can be constructed. Founder mice that are viable for most of these constructs can be identified, and breeding colonies can be developed. These mice will likely be prone to modulation of the serotonin-gated anion channel within tissue types in which the promoter is active. Thus the mice provide an excellent resource for testing the efficacy of antisense oligonucleotides, and for screening for therapeutics associated with serotonin-mediated cellular responses and the side-effects associated with these therapeutics. Standard mouse drug screening models and gene delivery protocols may be employed to utilize the mice for this purpose.

EXAMPLE 12

Characterization of mod-1 Mutants

A single base transition mutation in the mod-1 coding sequence in n3034 mutants was found. This missense mutation is predicted to change alanine 281 (codon GCT) to a valine (codon GTT) within the predicted M2 transmembrane domain of the MOD-1 protein (a domain thought to be critical for channel function). Site-directed mutagenesis was used to introduce this C-to-T (A281V) mutation into a 5.5 kb minimal fragment that rescues the mutant phenotype of serotonin resistance, and transgenic animals carrying extra-chromasomal arrays of the fragment, Ex[MOD-1(A281V)], were generated. These transgenic animals displayed resistance to exogenous serotonin, confirming that the C-to-T (A281V) change in the mod-1 locus was sufficient to cause serotonin resistance.

The effect on channel function of the MOD-1(A281V) substitution in the mod-1(n3034) mutant was also examined. When cRNA encoding MOD-1(A281V) was injected into oocytes, there were no serotonin-gated responses. When the mutant cRNA was co-injected with approximately a four-fold excess of wild-type mod-1 cRNA, the magnitude of the current through the wild-type channels was dramatically reduced compared to oocytes that had been injected in parallel with the same amount of only the wild-type cRNA. These findings indicate that the MOD-1 channel is multimeric and that mutant MOD-1 (A281V) channel subunits interfere in a dominant manner with the function of wild-type MOD-1 channel subunits.

To determine the phenotypic consequence of completely eliminating mod-1 function the deletion allele of mod-1, (ok103), was analyzed. This mutant was obtained by screening libraries of mutagenized animals using PCR to identify large deletions in the mod-1 genomic locus. mod-1(ok103) mutants, when food deprived, were defective in the enhanced slowing response, but was not defective in the basal slowing response displayed by well-fed wild-type animals. The deletion mutant was also resistant to exogenous serotonin. The serotonin resistance caused by the deletion allele was completely recessive throughout the 20 minute time course of serotonin exposure, which is consistent with our observation that animals heterozygous for large chromosomal deficiencies that uncover the mod-1 genomic locus are not serotonin resistant. The molecular nature of the mod-1(ok103) mutation suggests that it is a null allele. That null alleles confer the same phenotype as that conferred by the Ex[MOD-1(A281V)] extrachromosomal array suggests that mod-1 (n3034) is a dominant negative allele.

What is claimed is:

1. A substantially pure nucleic acid sequence encoding a serotonin-gated anion channel, wherein said nucleic acid sequence comprises the sequence of SEQ ID NO:2.

2. A substantially pure nucleic acid sequence encoding a serotonin-gated anion channel, wherein said serotonin-gated anion channel comprises the sequence of SEQ ID NO:3.

* * * * *

UNITED STATES PATENT AND TRADEMARK OFFICE
CERTIFICATE OF CORRECTION

| | |
|---|---|
| PATENT NO. | : 7,026,466 B1 |
| APPLICATION NO. | : 09/717743 |
| DATED | : April 11, 2006 |
| INVENTOR(S) | : Rajesh Ranganathan, H. Robert Horvitz and Stephen C. Cannon |

It is certified that error appears in the above-identified patent and that said Letters Patent is hereby corrected as shown below:

Column 14, Line 36, replace "*Xenopus oocytes*" with --*Xenopus* oocytes--.

Column 15, Line 63, replace "$Ca^{++}$" with --$Ca^{2+}$--.

Column 18, Line 48, replace "ooctye" with --oocyte--.

Column 20, Line 57, replace "*Xenopus oocyte*" with --*Xenopus* oocyte--.

Column 24,
    Line 6, replace "napthalenes" with --naphthalenes--; and
    Line 56, replace "chromasomal" with --chromosomal--.

Signed and Sealed this

Tenth Day of October, 2006

JON W. DUDAS
*Director of the United States Patent and Trademark Office*